(12) United States Patent
Ebi et al.

(10) Patent No.: US 9,075,005 B2
(45) Date of Patent: Jul. 7, 2015

(54) CELL ANALYZER AND CELL ANALYZING METHOD

(71) Applicant: Sysmex Corporation, Kobe-shi, Hyogo (JP)

(72) Inventors: Ryuichiro Ebi, Kobe (JP); Yousuke Tanaka, Kobe (JP); Junya Inoue, Kobe (JP); Shigeki Abe, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 13/963,157

(22) Filed: Aug. 9, 2013

(65) Prior Publication Data

US 2014/0051114 A1 Feb. 20, 2014

(30) Foreign Application Priority Data

Aug. 16, 2012 (JP) ................................. 2012-180631

(51) Int. Cl.
*G01N 21/47* (2006.01)
*G01N 15/14* (2006.01)

(52) U.S. Cl.
CPC ............ *G01N 21/47* (2013.01); *G01N 15/1468* (2013.01); *G01N 2015/1493* (2013.01)

(58) Field of Classification Search
CPC ..................... G01N 2333/00; G01N 2333/435; G01N 2800/00; G01N 2800/36; G01N 15/00; G01N 15/10; G01N 15/14; G01N 15/1404; G01N 2015/00; G01N 2015/10; G01N 2015/1006; G01N 2015/1497; C12Q 1/00; C12Q 2543/00; C12Q 2543/10; C12Q 2563/00; C12Q 2563/107
See application file for complete search history.

(56) References Cited

U.S. PATENT DOCUMENTS 6,143,512 A * 11/2000 Markovic et al. ............... 435/21
6,297,044 B1 10/2001 Eisen et al.
2002/0197723 A1 * 12/2002 Mason et al. .................... 436/63
2008/0108103 A1 5/2008 Ishisaka et al.
2011/0014685 A1 * 1/2011 Fukuda et al. .............. 435/286.2
2012/0148142 A1 * 6/2012 Ortyn et al. .................... 382/133

OTHER PUBLICATIONS

Cibas. 2002 (pre-print). Cervical and Vaginal Cytology. In: Cytology-Diagnostic Principles and Clinical Correlates. Saunders/Elsevier (publisher).Third edition. Copyright 2009 Elsevier Inc. Ed: Edmund S. Cibas and Barbara S. Ducatman. Philadelphia, PA. pp. 1-36). specif. pp. 1, 4, 8, 10-11.*
Arifler, D. et al. 2003. Light scattering from normal and dysplastic cervical cells at different epithelial depths: finite-difference time-domain modeling with a perfectly matched layer boundary condition. Journal of Biomedical Optics 8(3): 484-494. specif. pp. 484-485, 493.*
Becton, Dickinson and Company (BD). 2011. BD FocalPoint™ GS Imaging System. Product Insert. Copyright 2011. pp. 1-28. TriPath Imaging, Inc., Burlington, NC. specif. pp. 1-2, 8-9.*
The Merck Veterinary Manual. 2012. Cytology. Copyright 2010-2014. Merck, Sharp and Dohme Corp. Ed.: Last revised by Trevor J. Whitbread, Mar. 2012. Whitehouse Station, NJ. pp. 1-31). specif. p. 24.*
Garcia, G.L. et al. 1977. Ultrasonic disaggregation of cell clusters. Journal of Histochemistry and Cytochemistry 25(7): 508-512. specif. p. 508.*
Winter, M.J. et al. 2003. The epithelial cell adhesion molecule (Ep-CAM) as a morphoregulatory molecule is a tool in surgical pathology. American Journal of Pathology 163(6): 2139-2148. specif. pp. 2141, 2144 and 2145.*

* cited by examiner

*Primary Examiner* — John Brusca
*Assistant Examiner* — Sharon M Papciak
(74) *Attorney, Agent, or Firm* — Brinks Gilson & Lione

(57) ABSTRACT

Provided are a cell analyzer, and a cell analysis method. A cell analyzer 1 includes a measurement device 2 for detecting information of each cell from a measurement specimen containing cells harvested from an epithelial tissue, and a data processing device 3 for determining appropriateness of the cell harvesting of parabasal cells and acquiring information related to canceration of the cell based on the information detected by the measurement device 2. The data processing device 3 displays on a display section a dialogue showing "cell harvesting inappropriate" when determined that the harvesting of parabasal cells is inappropriate.

13 Claims, 19 Drawing Sheets

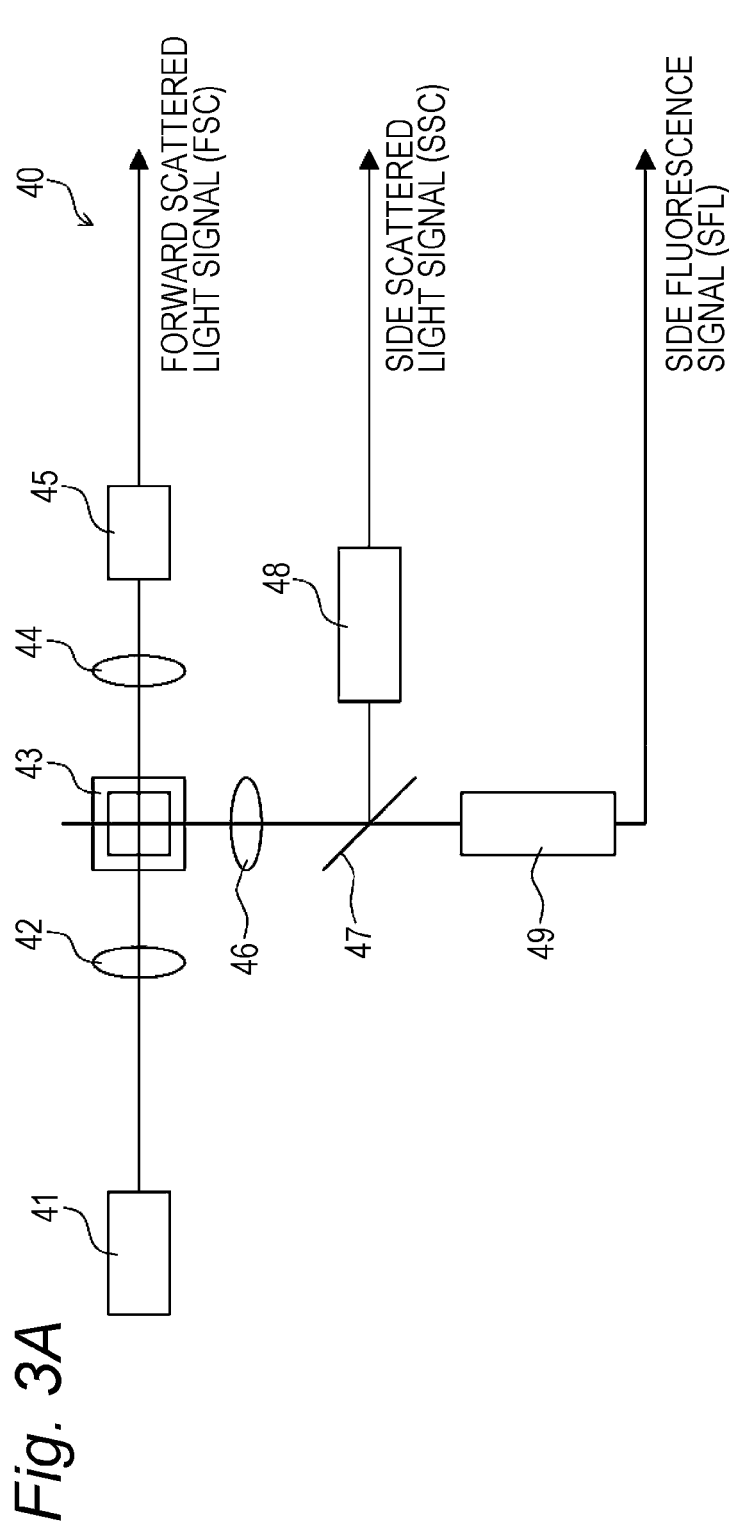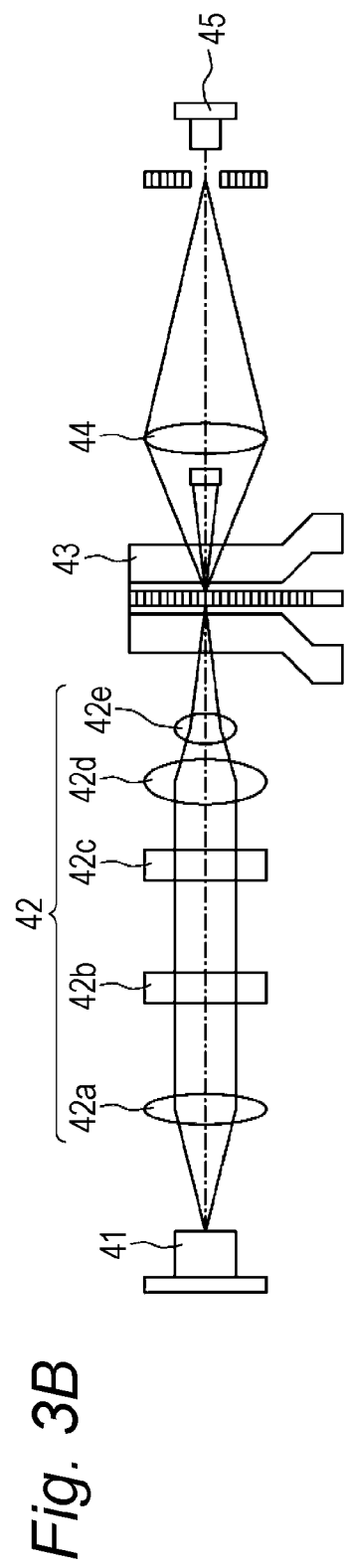

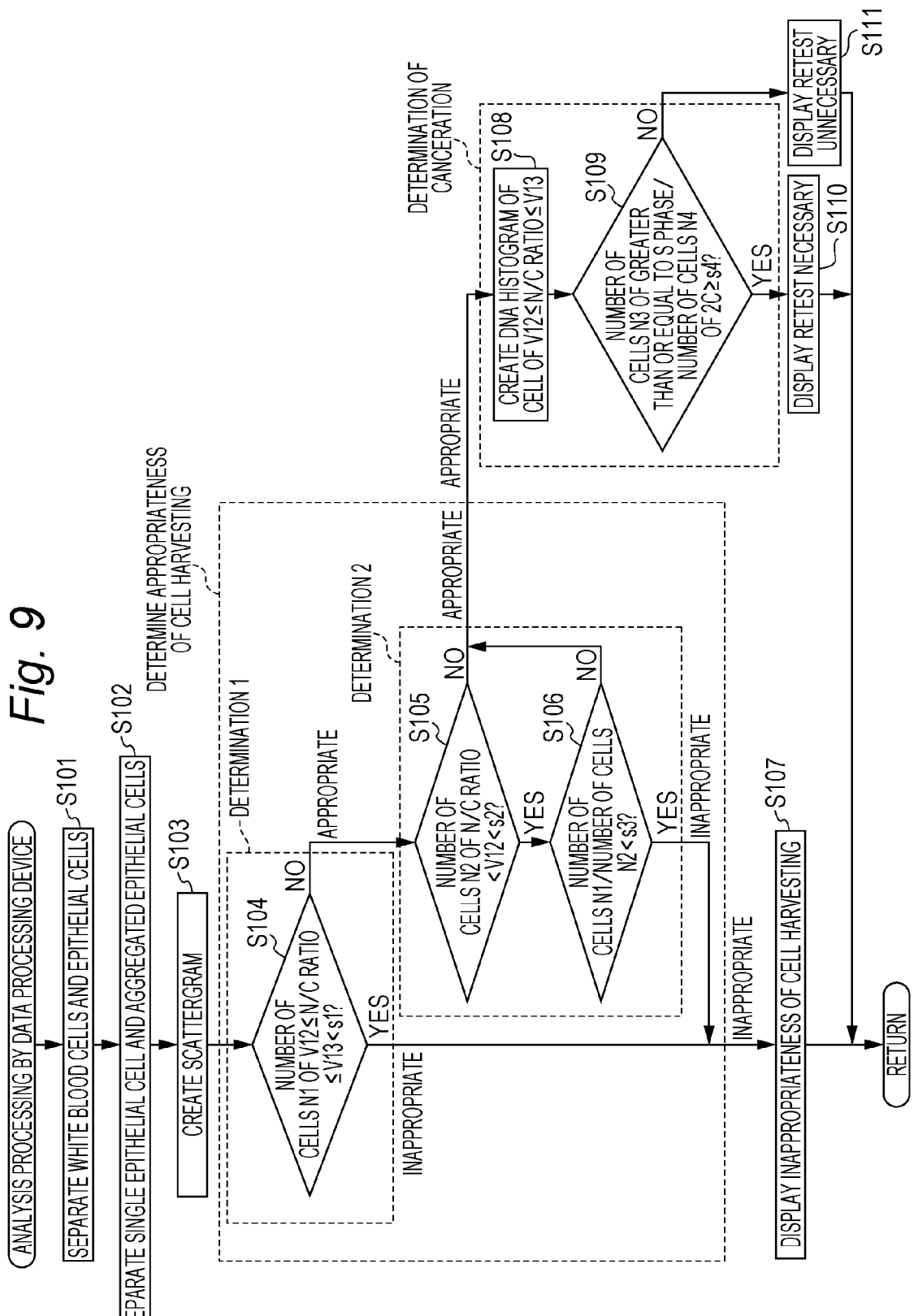

SAMPLE ID: 0001
"CELL HARVESTING INAPPROPRIATE"

SAMPLE ID: 0002
"RETEST NECESSARY"

SAMPLE ID: 0003
"RETEST UNNECESSARY"

SAMPLE ID: 0004
"LOW RELIABILITY"

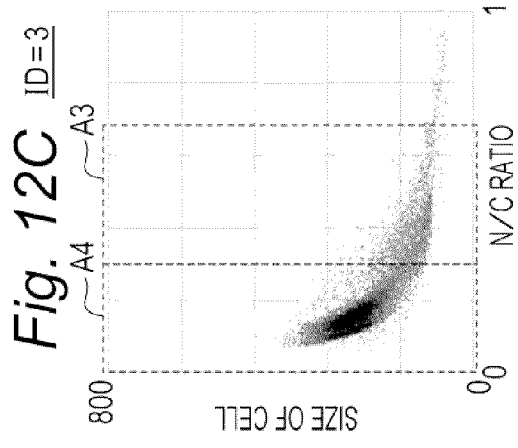
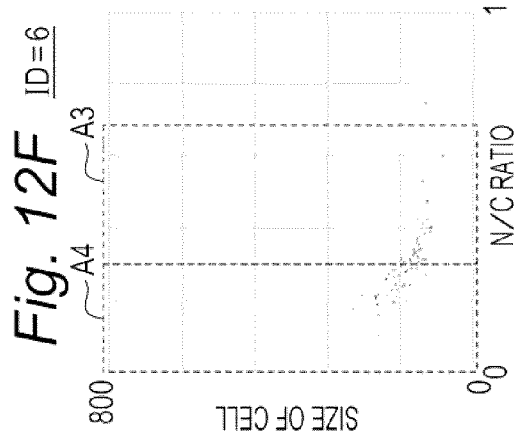
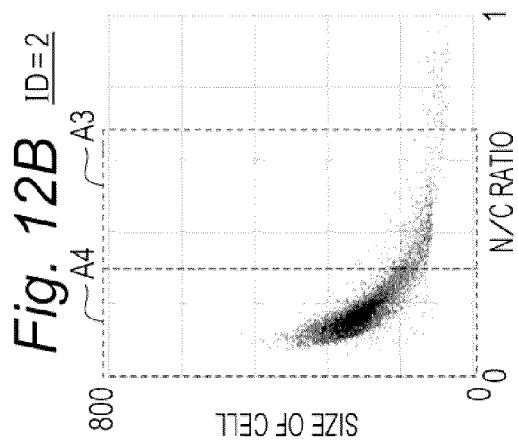
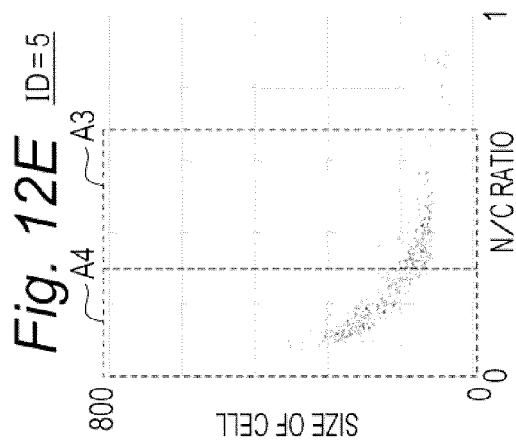
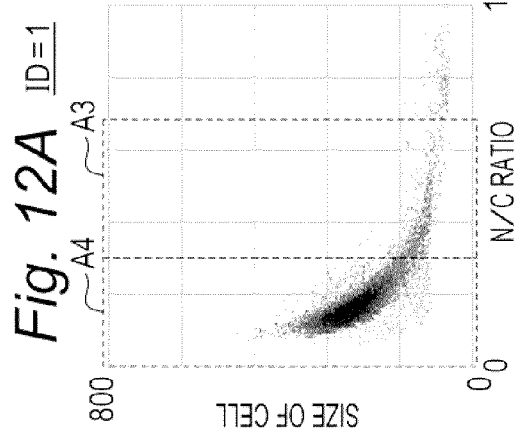
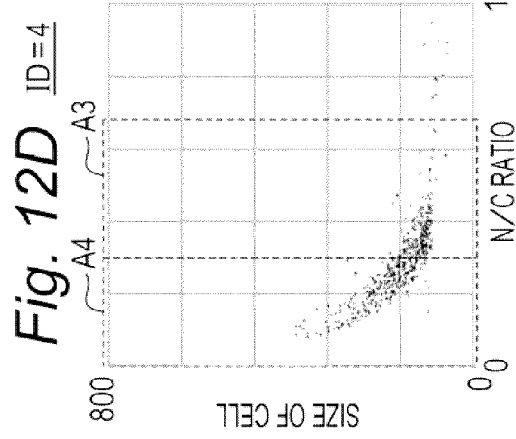

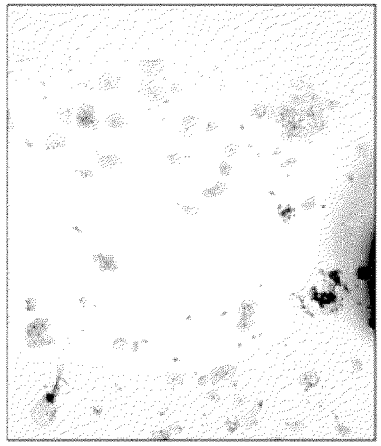
Fig. 13C  ID=3
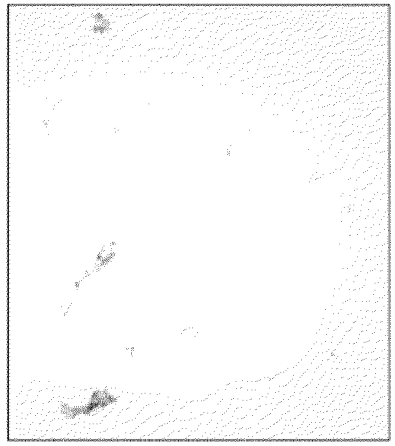
Fig. 13F  ID=6
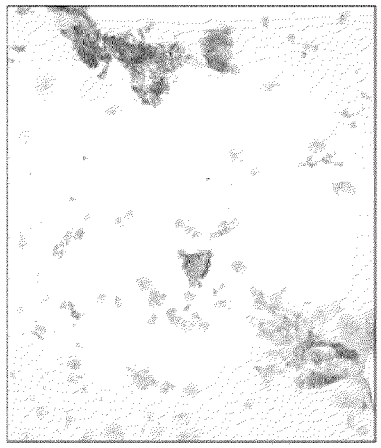
Fig. 13B  ID=2
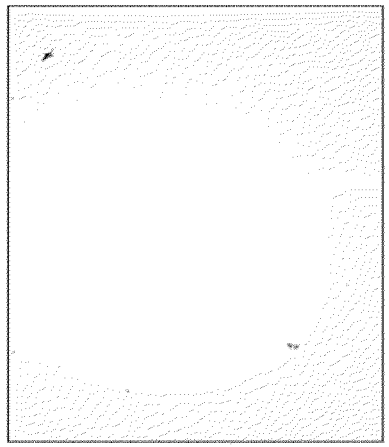
Fig. 13E  ID=5
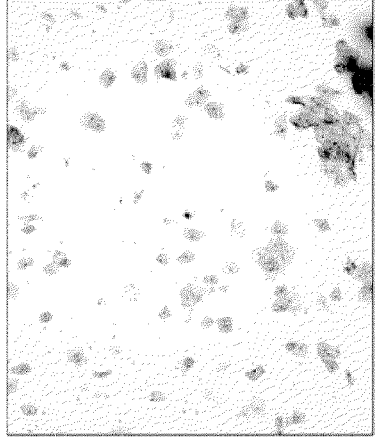
Fig. 13A  ID=1
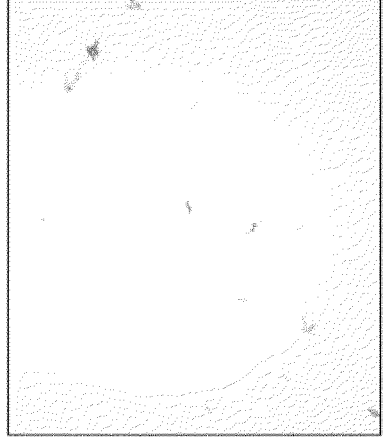
Fig. 13D  ID=4

Fig. 14A
ID=1

| DETERMINATION CONDITION | DETERMINATION ON APPROPRIATENESS OF CELL HARVESTING ACCORDING TO EMBODIMENT | | | OVERALL DETERMINATION | LBC APPROPRIATENESS DETERMINATION BETHESDA SYSTEM |
|---|---|---|---|---|---|
| | ITEM | DATA | DETERMINATION RESULT | | |
| 1 | N1 | 863 | APPROPRIATE | APPROPRIATE | APPROPRIATE |
| 2 | N2 | 20099 | APPROPRIATE | | |
| | N1/N2 | 0.07 | | | |

Fig. 14B
ID=2

| DETERMINATION CONDITION | DETERMINATION ON APPROPRIATENESS OF CELL HARVESTING ACCORDING TO EMBODIMENT | | | OVERALL DETERMINATION | LBC APPROPRIATENESS DETERMINATION BETHESDA SYSTEM |
|---|---|---|---|---|---|
| | ITEM | DATA | DETERMINATION RESULT | | |
| 1 | N1 | 904 | APPROPRIATE | APPROPRIATE | APPROPRIATE |
| 2 | N2 | 13768 | APPROPRIATE | | |
| | N1/N2 | 0.11 | | | |

Fig. 14C
ID=3

| DETERMINATION CONDITION | DETERMINATION ON APPROPRIATENESS OF CELL HARVESTING ACCORDING TO EMBODIMENT | | | OVERALL DETERMINATION | LBC APPROPRIATENESS DETERMINATION BETHESDA SYSTEM |
|---|---|---|---|---|---|
| | ITEM | DATA | DETERMINATION RESULT | | |
| 1 | N1 | 2959 | APPROPRIATE | APPROPRIATE | APPROPRIATE |
| 2 | N2 | 30776 | APPROPRIATE | | |
| | N1/N2 | 0.12 | | | |

Fig. 14D
ID = 4

| DETERMINATION CONDITION | DETERMINATION ON APPROPRIATENESS OF CELL HARVESTING ACCORDING TO EMBODIMENT | | | OVERALL DETERMINATION | LBC APPROPRIATENESS DETERMINATION BETHESDA SYSTEM |
|---|---|---|---|---|---|
| | ITEM | DATA | DETERMINATION RESULT | | |
| 1 | N1 | 227 | INAPPROPRIATE | INAPPROPRIATE | INAPPROPRIATE |
| 2 | N2 | 618 | APPROPRIATE | | |
| | N1/N2 | 1.09 | | | |

Fig. 14E
ID = 5

| DETERMINATION CONDITION | DETERMINATION ON APPROPRIATENESS OF CELL HARVESTING ACCORDING TO EMBODIMENT | | | OVERALL DETERMINATION | LBC APPROPRIATENESS DETERMINATION BETHESDA SYSTEM |
|---|---|---|---|---|---|
| | ITEM | DATA | DETERMINATION RESULT | | |
| 1 | N1 | 179 | INAPPROPRIATE | INAPPROPRIATE | INAPPROPRIATE |
| 2 | N2 | 513 | APPROPRIATE | | |
| | N1/N2 | 1.02 | | | |

Fig. 14F
ID = 6

| DETERMINATION CONDITION | DETERMINATION ON APPROPRIATENESS OF CELL HARVESTING ACCORDING TO EMBODIMENT | | | OVERALL DETERMINATION | LBC APPROPRIATENESS DETERMINATION BETHESDA SYSTEM |
|---|---|---|---|---|---|
| | ITEM | DATA | DETERMINATION RESULT | | |
| 1 | N1 | 39 | INAPPROPRIATE | INAPPROPRIATE | INAPPROPRIATE |
| 2 | N2 | 88 | APPROPRIATE | | |
| | N1/N2 | 1.42 | | | |

Fig. 16A

| DETERMINATION 1 | | CYTOLOGICAL DIAGNOSIS AND TISSUE DIAGNOSIS | |
|---|---|---|---|
| | | POSITIVE | NEGATIVE |
| DETERMINATION OF CANCERATION | POSITIVE | 55 | 159 |
| | NEGATIVE | 2 | 828 |
| TOTAL | | 57 | 987 |
| NUMBER OF INAPPROPRIATE SAMPLES | | 72 | |
| RATE OF INAPPROPRIATE SAMPLES | | 6.9% | |

Fig. 16B

| DETERMINATION 1 | | CYTOLOGICAL DIAGNOSIS AND TISSUE DIAGNOSIS | |
|---|---|---|---|
| | | POSITIVE | NEGATIVE |
| DETERMINATION OF CANCERATION | POSITIVE | 96.5% | 16.1% |
| | NEGATIVE | 3.5% | 83.9% |
| SORT OUT RATE | | 74.2% | |

Fig. 16C

| DETERMINATION 1 + DETERMINATION 2 | | CYTOLOGICAL DIAGNOSIS AND TISSUE DIAGNOSIS | |
|---|---|---|---|
| | | POSITIVE | NEGATIVE |
| DETERMINATION OF CANCERATION | POSITIVE | 52 | 149 |
| | NEGATIVE | 1 | 792 |
| TOTAL | | 53 | 941 |
| NUMBER OF INAPPROPRIATE SAMPLES | | 122 | |
| RATE OF INAPPROPRIATE SAMPLES | | 12.3% | |

Fig. 16D

| DETERMINATION 1 + DETERMINATION 2 | | CYTOLOGICAL DIAGNOSIS AND TISSUE DIAGNOSIS | |
|---|---|---|---|
| | | POSITIVE | NEGATIVE |
| DETERMINATION OF CANCERATION | POSITIVE | 98.1% | 15.8% |
| | NEGATIVE | 1.9% | 84.2% |
| SORT OUT RATE | | 71.0% | |

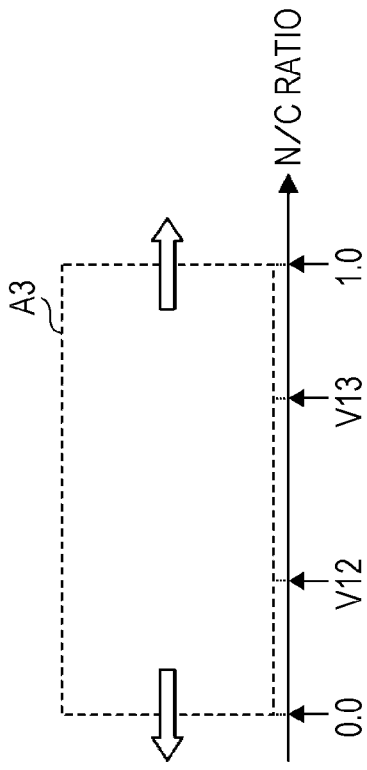
Fig. 18A  PATTERN 1
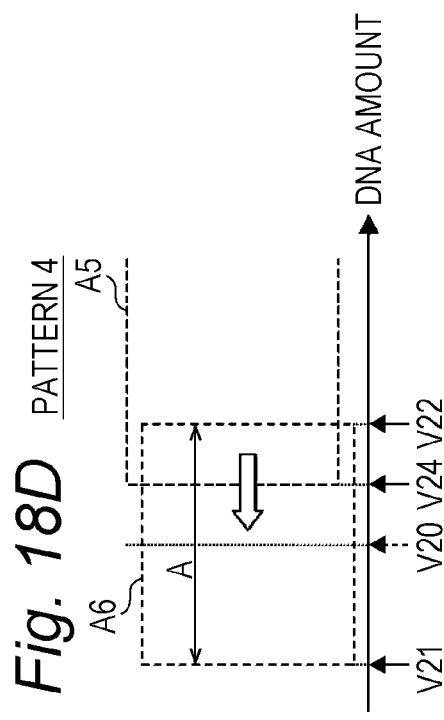
Fig. 18B  PATTERN 2
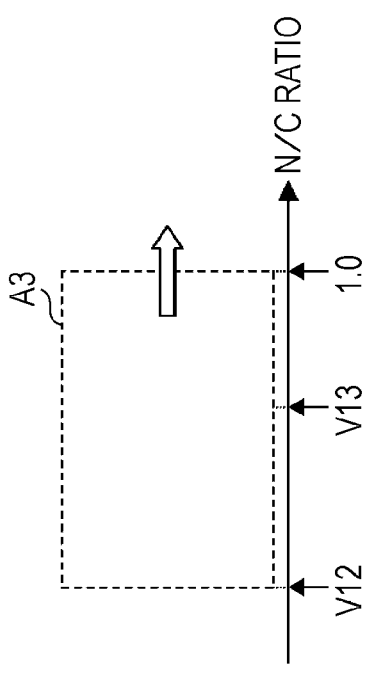
Fig. 18C  PATTERN 3
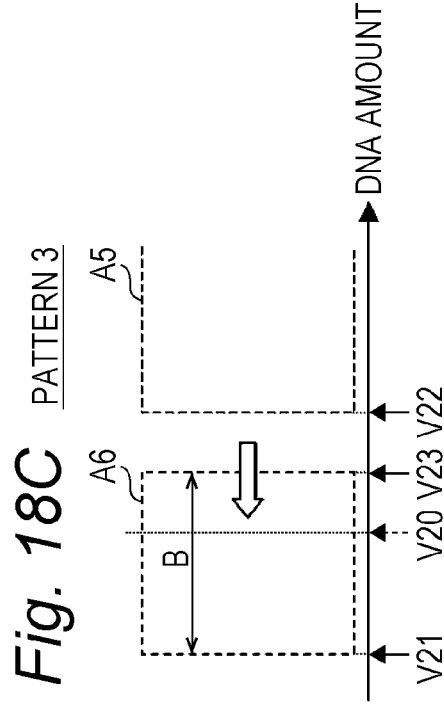
Fig. 18D  PATTERN 4

CELL ANALYZER AND CELL ANALYZING METHOD

RELATED APPLICATIONS

This application claims priority under 35 U.S.C. §119 to Japanese Patent Application No. 2012-180631 filed on Aug. 16, 2012, the entire content of which is hereby incorporated by reference.

BACKGROUND OF THE INVENTION

1. Field of the Invention

The present invention relates to a cell analyzer, and a cell analyzing method.

2. Description of the Related Art

An analyzer for automatically analyzing the cells of the subject, and providing information related to canceration of the relevant cells (see e.g., US2008-108103A1). US2008-108103A1 discloses a device for flowing a measurement specimen containing the cells harvested from the subject to a flow cell, irradiating light on the measurement specimen flowing through the flow cell to acquire a scattered light signal for the individual cell, extracting a feature parameter by analyzing the waveform of each scattered light signal, and discriminating cancer/atypical cells from a plurality of cells using the feature parameter.

A basal layer, a parabasal layer, an intermediate layer, and a surface layer are formed in order from the basement membrane side in a uterine cervix. In the tissue diagnosis of the uterine cervix, the process from the normal state to canceration includes a plurality of stages of "Normal", "CIN1", "CIN2", "CIN3", and "Cancer" in order from the normal state. "CIN1" is a state in which the atypical cell is growing in one third from the basal layer toward the surface layer, "CIN2" is a state in which the atypical cell is growing in two thirds from the basal layer toward the surface layer, and "CIN3" is a state in which the atypical cell is growing over substantially entirely from the basal layer to the surface layer. In the process of becoming cancer, the basal cell acquires dysplasia and becomes the atypical cell. The atypical cell acquires the growth ability, and occupies from the basal layer side to the surface layer side. Thus, precancerous lesion appears in the early stage on the basal cell side.

The basal cell of the uterine cervix is the bottommost layer of the epidermis and therefore difficult to collect, and such collection involves pain to the subject, and thus the basal cells are not generally harvested. Therefore, the epidermal cells of the uterine cervix that can be harvested from the subject include the parabasal cell, the intermediate layer cell, and the surface layer cell. In other words, in the process in which the cancer progresses in the epidermal cells that can be harvested, the precancerous lesion appears at an early stage in the parabasal cell.

In order to start the treatment of cancer at an early stage, detection of the precancerous lesion is desirable at an initial stage of cancer such as from "CIN2" to "CIN3". However, in the conventional analyzer such as the analyzer described in US. Application Publication No. 2008/108103A, the possibility of precancerous lesion and cancer may not be appropriately determined unless the collection of cells useful in the determination of the precancerous lesion is appropriately carried out at the time of harvesting the epithelial tissue from the uterine cervix.

SUMMARY OF THE INVENTION

A first aspect of the present invention relates to a cell analyzer. The analyzer comprises a detecting section for detecting information of each cell from a measurement specimen containing cells harvested from an epithelial tissue, and an information processing section for determining appropriateness of the cell harvesting of parabasal cells based on the information detected by the detecting section.

A second aspect of the present invention relates to a cell analyzer. The cell analyzer according to the present aspect is used for determining whether or not cells useful in the determination of canceration are appropriately harvested and contained in a measurement specimen. The appropriateness of cell harvesting of parabasal cells is determined based on information of each cell detected from the measurement specimen containing cells harvested from an epithelial tissue.

A third aspect of the present invention relates to a cell analyzing method for determining whether or not cells useful in the determination of canceration are appropriately harvested and contained in a measurement specimen. In this method, detected is information of each cell from the measurement specimen containing cells harvested from an epithelial tissue, and determined is appropriateness of the cell harvesting of parabasal cells based on the detected information.

BRIEF DESCRIPTION OF THE DRAWINGS

FIGS. 3A and 3B are diagrams showing a configuration of a flow cytometer according to the embodiment;

FIG. 9 is a flowchart showing analysis processing in the data processing device according to the embodiment;

FIGS. 12A to 12F are graphs showing specific examples of the scattergrams generated by the analysis processing according to the embodiment;

FIGS. 13A to 13F are images showing slides created in cytological diagnosis;

FIGS. 14A to 14F are tables showing simulation results of the determination on the appropriateness of cell harvesting according to the embodiment;

FIGS. 16A to 16D are tables showing determination results of canceration and determination results of tissue diagnosis according to the modifications and the embodiment;

FIGS. 18A to 18D are diagrams showing regions set in the scattergram and the histogram according to the modifications.

DETAILED DESCRIPTION OF THE PREFERRED EMBODIMENT

The description on the correspondence of the claims and the present embodiment is merely an example, and the invention according to the claims is not to be limited to the present embodiment.

The canceration information providing device 1 flows a measurement specimen containing cells (biological specimen) harvested from a patient (subject) through a flow cell, and irradiates a laser light on the measurement specimen flowing through the flow cell. Whether or not the cells contain cancerous cells or cells in the process of canceration (hereinafter also collectively referred to as "neoplastic cells") is determined by detecting light (forward scattered light, side scattered light, side fluorescence) from the measurement specimen and analyzing the light signals. Specifically, the canceration information providing device 1 is used in screening a uterine cervix cancer using epidermal cells of the uterine cervix harvested from the patient.

Figure 1:
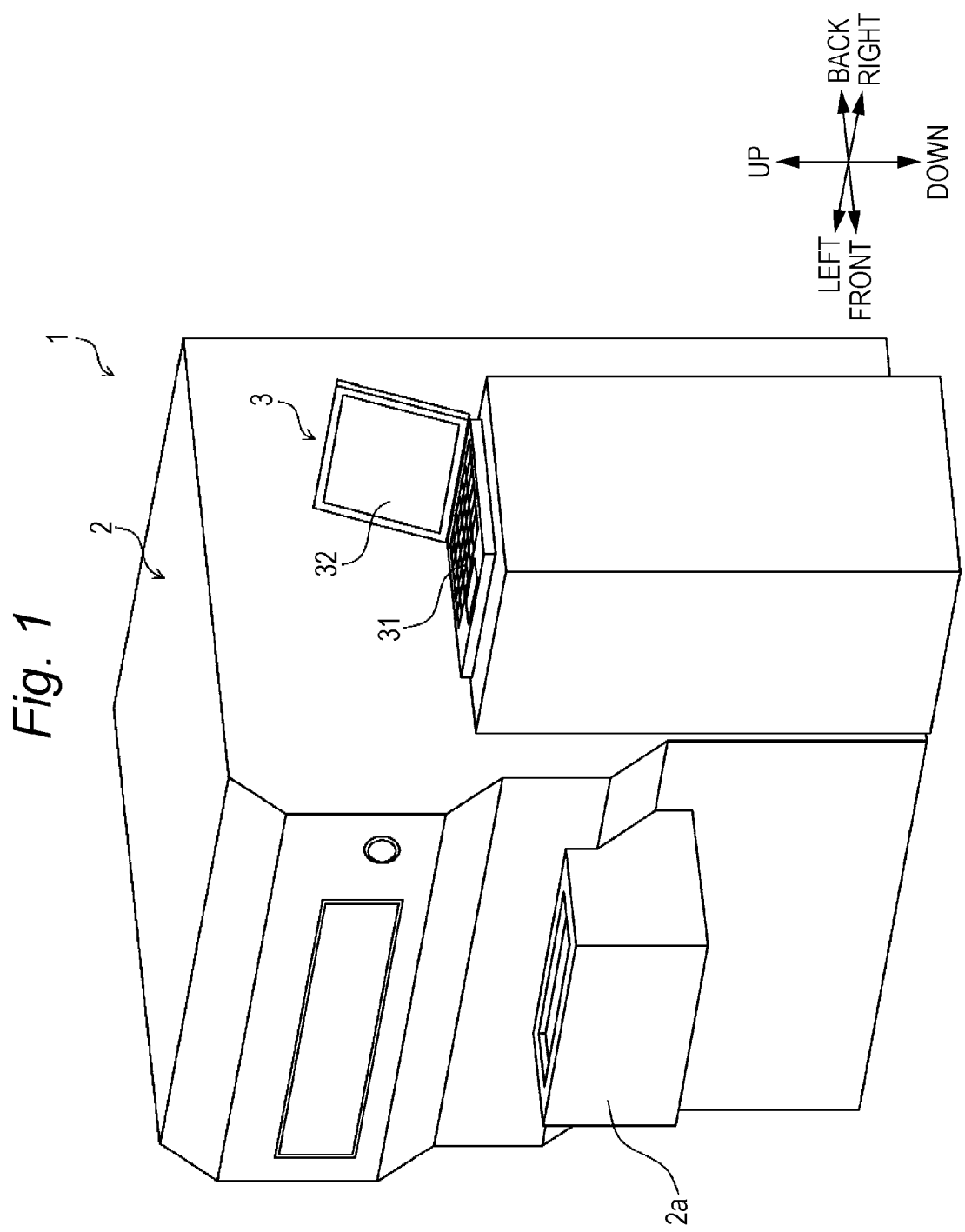
FIG. 1 is a perspective view schematically showing a configuration of an outer appearance of a canceration information providing device according to an embodiment.

As shown in FIG. 1, the canceration information providing device 1 includes the measurement device 2 for performing measurement and the like of the biological specimen collected from the patient, and the data processing device 3, connected to the measurement device 2, for performing analysis, display (output) and the like of the measurement result. On a front surface of the measurement device 2 is installed a sample setting section 2a for setting a plurality of specimen containers 4 (see FIG. 2) for accommodating a mixed solution (specimen) of a preservation solution, of which a main component is methanol, and the biological specimen collected from the patient. The data processing device 3 includes an input section 31 and the display section 32.

Figure 2:
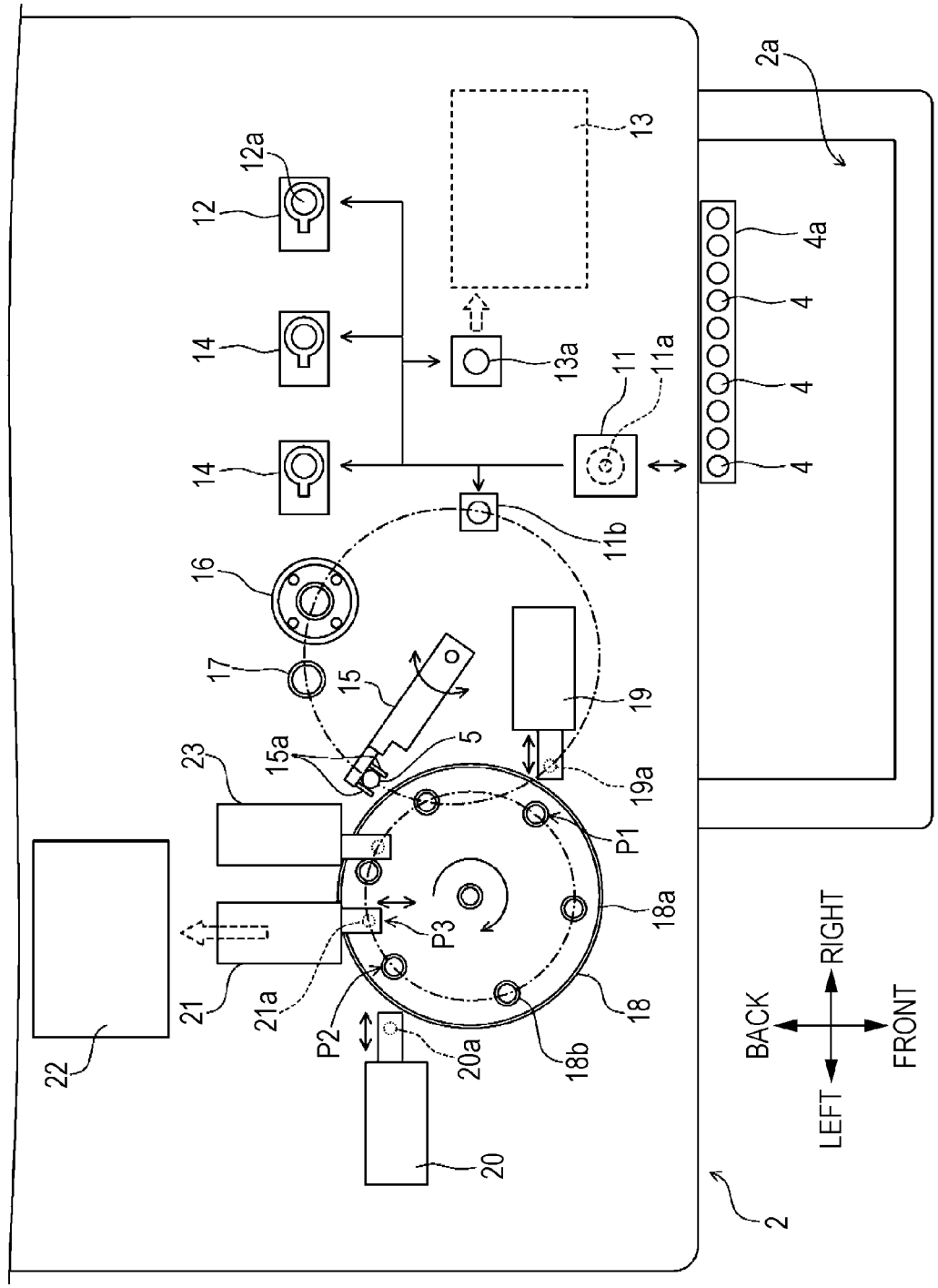
FIG. 2 is a plan view schematically showing a configuration of the inside of a measurement device according to the embodiment.

As shown in FIG. 2, the sample setting section 2a sequentially transports a rack 4a, in which the plurality of specimen containers 4 is set, to an aspirating position in which a sample pipette section 11 aspirates the specimen.

The sample pipette section 11 transfers the specimen in the specimen container 4 to the first dispersion section 12. The sample pipette section 11 also transfers the specimen in the first dispersion section 12 to a sub-detecting section 13 and a discriminating/replacing section 14. The sample pipette section 11 further supplies a concentrated solution concentrated in the discriminating/replacing section 14 to a measurement specimen container 5. The sample pipette section 11 is configured to be movable to upper positions of a specimen accommodating unit 12a of the first dispersion section 12, a specimen retrieving unit 13a of the sub-detecting section 13, the discriminating/replacing section 14, and the measurement specimen container 5 positioned in a specimen exchanging section 11b.

The sample pipette section 11 includes a pipette 11a for aspirating and discharging the specimen, and is configured to determine the quantity of the specimen by a sample quantifying section (quantifying cylinder, motor for driving a piston in the quantifying cylinder, etc.) (not shown) and supply a predetermined amount of the specimen to each section described above.

The first dispersion section 12 performs on the specimen first dispersion treatment of dispersing the aggregated cells contained in the specimen. Specifically, the first dispersion treatment is shearing force applying processing of dispersing the aggregated cells by applying the shearing force on the aggregated cells. The first dispersion section 12 includes the specimen accommodating unit 12a capable of accommodating the specimen, and is configured to mechanically apply the shearing force on the aggregated cells in the specimen supplied to the specimen accommodating unit 12a.

The sub-detecting section 13 performs concentration measurement of the specimen before the actual measurement by a main detecting section 22. The sub-detecting section 13 adopts a flow cytometer 40 (see FIG. 3A) having substantially the same configuration as the main detecting section 22, to be described later.

The discriminating/replacing section 14 receives the specimen having undergone the first dispersion treatment by the first dispersion section 12, and replaces the preservation solution, of which a main component is methanol, contained in the specimen with a diluted solution. The discriminating/replacing section 14 also discriminates cells to be measured (epidermal cells, gland cells of uterine cervix) contained in the specimen, and other cells (red blood cells, white blood cells, bacteria, etc.) as well as foreign substances. The discriminating/replacing section 14 also performs concentration of the cells to be measured contained in the specimen to obtain the number of cell measurements necessary in the measurement by the main detecting section 22. Two discriminating/replacing sections 14 are provided to make the processing more efficient.

A container transfer section 15 grips the measurement specimen container 5 set in a reaction section 18 with a scissor-like gripping unit 15a and transfers the same to the specimen exchanging section 11b, the second dispersion section 16, a liquid removing section 17, and the reaction section 18. The container transfer section 15 is configured to move the gripping unit 15a along a predetermined circumferential path. The container transfer section 15 is also configured so as to be able to move the gripping unit 15a in a vertical direction. The specimen exchanging section 11b, the second dispersion section 16, the liquid removing section 17, and the reaction section 18 are arranged on the circumferential path. The measurement specimen container 5 set in the reaction section 18 thus can be transferred to each section on the circumferential path by being gripped by the gripping unit 15a of the container transfer section 15.

The second dispersion section 16 performs a second dispersion treatment, which is different from the first dispersion treatment, on the specimen having undergone the first dispersion treatment performed by the first dispersion section 12. Specifically, the second dispersion section 16 is configured to apply an ultrasonic vibration on the specimen having undergone the first dispersion treatment performed by the first dispersion section 12 and concentrated (concentration of the cell to be measured is increased) in the discriminating/replacing section 14. The aggregated cells remaining after the first dispersion treatment are dispersed into single cells by the second dispersion section 16.

The liquid removing section 17 removes (drains) liquid attached to the outer surface of the measurement specimen container 5 after the second dispersion treatment by the second dispersion section 16. The second dispersion treatment is performed in a state the measurement specimen container 5 is immersed in liquid. The liquid removing section 17 is configured to remove water droplets attached to the outer surface of the measurement specimen container 5 by supplying air flow to the outer surface of the measurement specimen container 5. Thus, when the measurement specimen container 5 is set in each section such as the reaction section 18, the attachment of liquid to each section can be prevented.

The reaction section 18 promotes the reaction between the specimen in the measurement specimen container 5 and reagents added by a first reagent adding section 19 and a second reagent adding section 20. The reaction section 18 includes a circular rotating table 18a configured to be rotatable by a drive section (not shown). On an outer circumferential edge of the rotating table 18a is arranged a plurality of holders 18b to which the measurement specimen container 5 can be set. The measurement specimen container 5 is set in the holder 18b. A path of the holder 18b obtained by the rotation of the rotating table 18a and the circumferential path of the gripping unit 15a of the container transfer section 15 intersect at a predetermined position, where the container transfer section 15 can set the measurement specimen container 5 in the holder 18b at such an intersection position. The reaction section 18 warms the measurement specimen container 5 set in the holder 18b to a predetermined temperature (about 37 degrees) to promote the reaction between the specimen and the reagent.

The first reagent adding section 19 and the second reagent adding section 20 supply the reagents into the measurement specimen container 5 set in the holder 18b. The first reagent adding section 19 and the second reagent adding section 20 are installed at positions in the vicinity of a circumferential edge of the rotating table 18a, and include supplying units 19a, 20a, respectively, that can be moved to each of positions P1, P2 on the upper side of the measurement specimen container 5 set in the rotating table 18a. Thus, when the measurement specimen container 5 is transported to the positions P1, P2 by the rotating table 18a, a predetermined amount of the reagents can be added into the measurement specimen container 5 from the supplying units 19a, 20a.

The reagent added by the first reagent adding section 19 is RNase for performing RNA removal processing on the cell. The reagent added by the second reagent adding section 20 is a stain solution for performing DNA stain treatment on the cell. According to the RNA removal processing, the RNA in the cell is broken down so that only the DNA of the cell nucleus can be measured. The DNA stain treatment is performed with propidium iodide (PI), which is a fluorescent stain solution containing pigment. According to the DNA stain treatment, the nucleus in the cell is selectively stained. The fluorescence from the nucleus then can be detected.

A specimen aspirating section 21 aspirates the specimen (measurement specimen) in the measurement specimen container 5 set in the holder 18b and transfers the aspirated measurement specimen to the main detecting section 22. The specimen aspirating section 21 is installed at a position in the vicinity of the circumferential edge of the rotating table 18a, and includes a pipette 21a that can be moved to a position P3 on the upper side of the measurement specimen container 5 set in the rotating table 18a. Thus, when the measurement specimen container 5 is transported to the position P3 by the rotating table 18a, the specimen aspirating section 21 can aspirate the measurement specimen in the measurement specimen container 5. The specimen aspirating section 21 is also connected to a flow cell 43 (see FIG. 3A) of the main detecting section 22 by way of a flow path (not shown), and is configured so that the measurement specimen aspirated by the pipette 21a can be supplied to the flow cell 43 of the main detecting section 22.

The main detecting section 22 includes the flow cytometer 40 for detecting the light from the measurement specimen, and outputs the signal based on each light to a post-stage circuit. The Examples of the light are scattered light and fluorescence. The Examples of the scattered light are forward scattered light and side scattered light. The flow cytometer 40 will be described later with reference to FIGS. 3A and 3B.

A container washing section 23 washes the inside of the measurement specimen container 5 after the measurement specimen is supplied to the main detecting section 22 by the specimen aspirating section 21. The container washing section 23 discharges a washing solution into the measurement specimen container 5 held in the holder 18b of the rotating table 18a to wash the inside of the measurement specimen container 5. Thus, contamination with other specimens can be suppressed when the same measurement specimen container 5 is used in the subsequent measurement processing.

FIG. 3A is a diagram showing a configuration of the flow cytometer 40 of the main detecting section 22. As shown in FIGS. 3A and 3B, the laser light exit from a semiconductor laser 41 is collected on the measurement specimen flowing through the flow cell 43 by a lens system 42, which includes a plurality of lenses. As described above, the specimen aspirated by the pipette 21a of the specimen aspirating section 21 is supplied to the flow cell 43.

As shown in FIG. 3B, the lens system 42 is configured by a collimator lens 42a, a cylinder lens system (plane convex cylinder lens 42b and biconcave cylinder lens 42c), and a condenser lens system (condenser lens 42d and condenser lens 42e), which are arranged in order from the semiconductor laser 41 side (left side of FIGS. 3A, 3B).

A light collecting lens 44 collects the forward scattered light of the cells in the measurement specimen to a scattered light detector including a photodiode 45. A light collecting lens 46 for side light collects the side scattered light and the side fluorescence of the cell to be measured and the nucleus in the cell, and guides the light to a dichroic mirror 47. The dichroic mirror 47 reflects the side scattered light toward a photomultiplier 48 and transmits the side fluorescence toward a photomultiplier 49. The side scattered light is collected in the photomultiplier 48, and the side fluorescence is collected in the photomultiplier 49 in such a manner. Such lights reflect the characteristics of the cell and the nucleus in the measurement specimen.

The photodiode 45 and the photomultipliers 48, 49 convert the received light signal to an electric signal, and output a forward scattered light signal (FSC), a side scattered light signal (SSC), and a side fluorescence signal (SFL), respectively. Such output signals are amplified by an amplifier (not shown), and output to a signal processing section 24 (see FIG. 4) of the measurement device 2.

Figure 4:
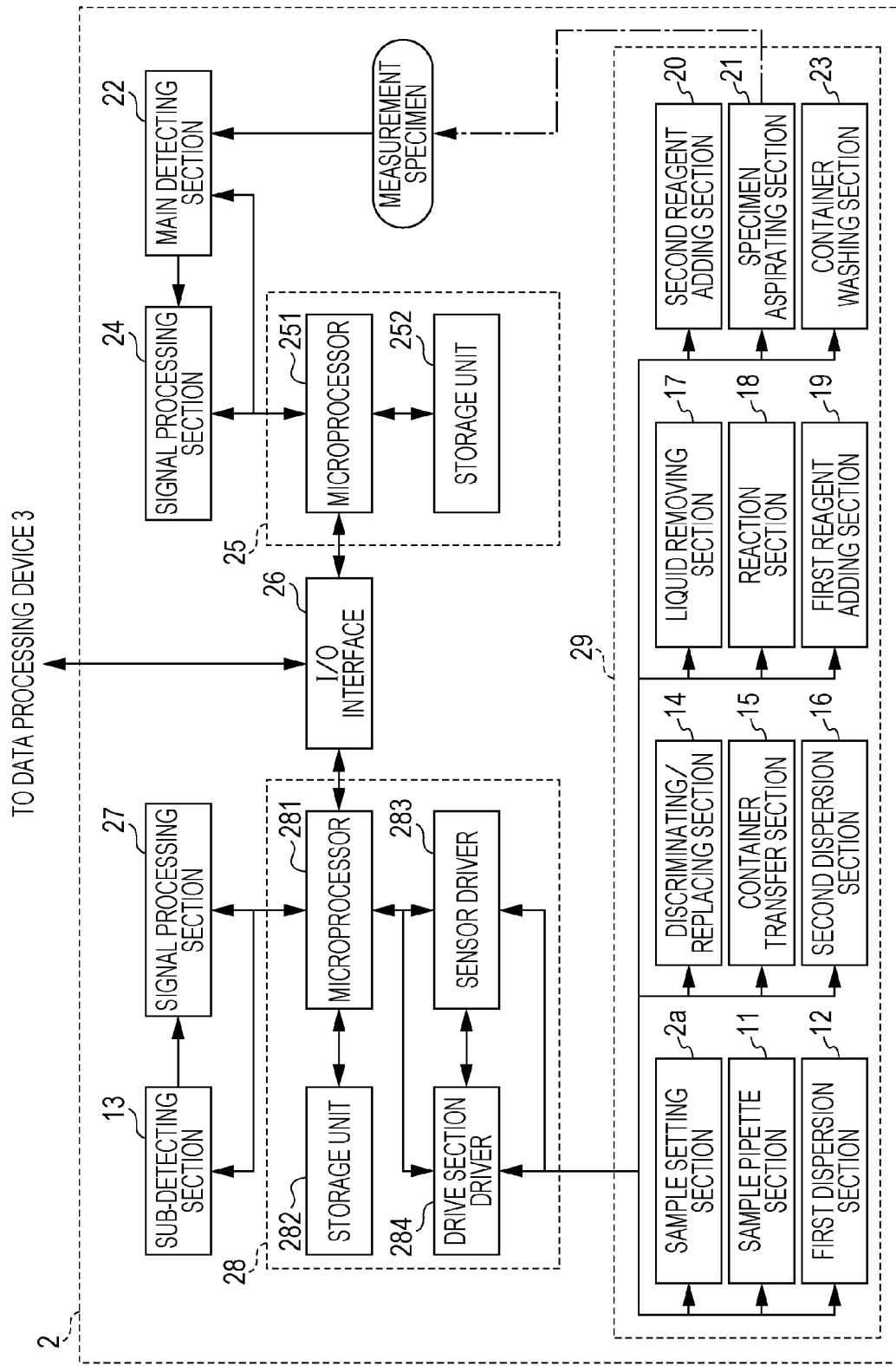
FIG. 4 is a diagram showing a configuration of the measurement device according to the embodiment.

As shown in FIG. 4, the measurement device 2 includes the main detecting section 22 shown in FIG. 2, the sub-detecting section 13, and a preparation device section 29 including each sections for automatically performing component adjustment on the specimen as described above. The measurement device 2 also includes the signal processing section 24, a measurement control section 25, an I/O interface 26, a signal processing section 27, and a preparation control section 28.

As described above, the main detecting section 22 includes the flow cytometer 40 shown in FIG. 3A, and outputs the forward scattered light signal (FSC), the side scattered light signal (SSC), and the side fluorescence signal (SFL) from the measurement specimen. The signal processing section 24 includes a signal processing circuit for performing necessary signal processing on the output signal from the main detecting section 22, and processes each signal FSC, SSC, SFL output from the main detecting section 22 and outputs the same to the measurement control section 25.

The measurement control section 25 includes a microprocessor 251 and a storage unit 252. The microprocessor 251 is connected to the data processing device 3 and the microprocessor 281 of the preparation control section 28 by way of the I/O interface 26. The microprocessor 251 thus can transmit and receive various types of data to and from the data processing device 3 and the microprocessor 281 of the preparation control section 28. The storage unit 252 includes a ROM for storing a control program and data of the main detecting section 22 and the like, a RAM, and the like.

Each signal FSC, SSC, SFL processed by the signal processing section 24 of the measurement device 2 are transmitted from the I/O interface 26 to the data processing device 3 by the microprocessor 251.

The sub-detecting section 13 adopts the flow cytometer 40 having substantially the same configuration as the main detecting section 22, and thus the description on the configuration will be omitted. The sub-detecting section 13 performs concentration measurement of the specimen before the actual measurement by the main detecting section 22. In the present embodiment, the sub-detecting section 13 is configured to acquire the forward scattered light signal (FSC), and outputs a signal for counting the number of cells having a size corresponding to a surface layer cell and an intermediate layer cell based on the forward scattered light signal. The signal processing section 27 includes a signal processing circuit for performing necessary signal processing on the output signal from the sub-detecting section 13, and processes the forward scattered light signal FSC output from the sub-detecting section 13 and outputs the same to the preparation control section 28.

The preparation control section 28 includes the microprocessor 281, a storage unit 282, a sensor driver 283, and a drive section driver 284. The microprocessor 281 is connected to the microprocessor 251 of the measurement control section 25 by way of the I/O interface 26. The microprocessor 281 thus can transmit and receive various types of data with the microprocessor 251 of the measurement control section 25.

The storage unit 282 includes a ROM for storing a control program, and the like for controlling the sub-detecting section 13 and the preparation device section 29 and the like, a RAM, and the like. The preparation device section 29 includes the sample setting section 2a, the sample pipette section 11, the first dispersion section 12, the discriminating/replacing section 14, the container transfer section 15, the second dispersion section 16, the liquid removing section 17, the reaction section 18, the first reagent adding section 19, the second reagent adding section 20, the specimen aspirating section 21, and the container washing section 23 shown in FIG. 2.

The microprocessor 281 is connected to sensors and drive motors of each section of the preparation device section 29 by way of the sensor driver 283 or the drive section driver 284. The microprocessor 281 thus can execute the control program based on the detection signals from the sensors, and control the operation of the drive motor.

Figure 5:
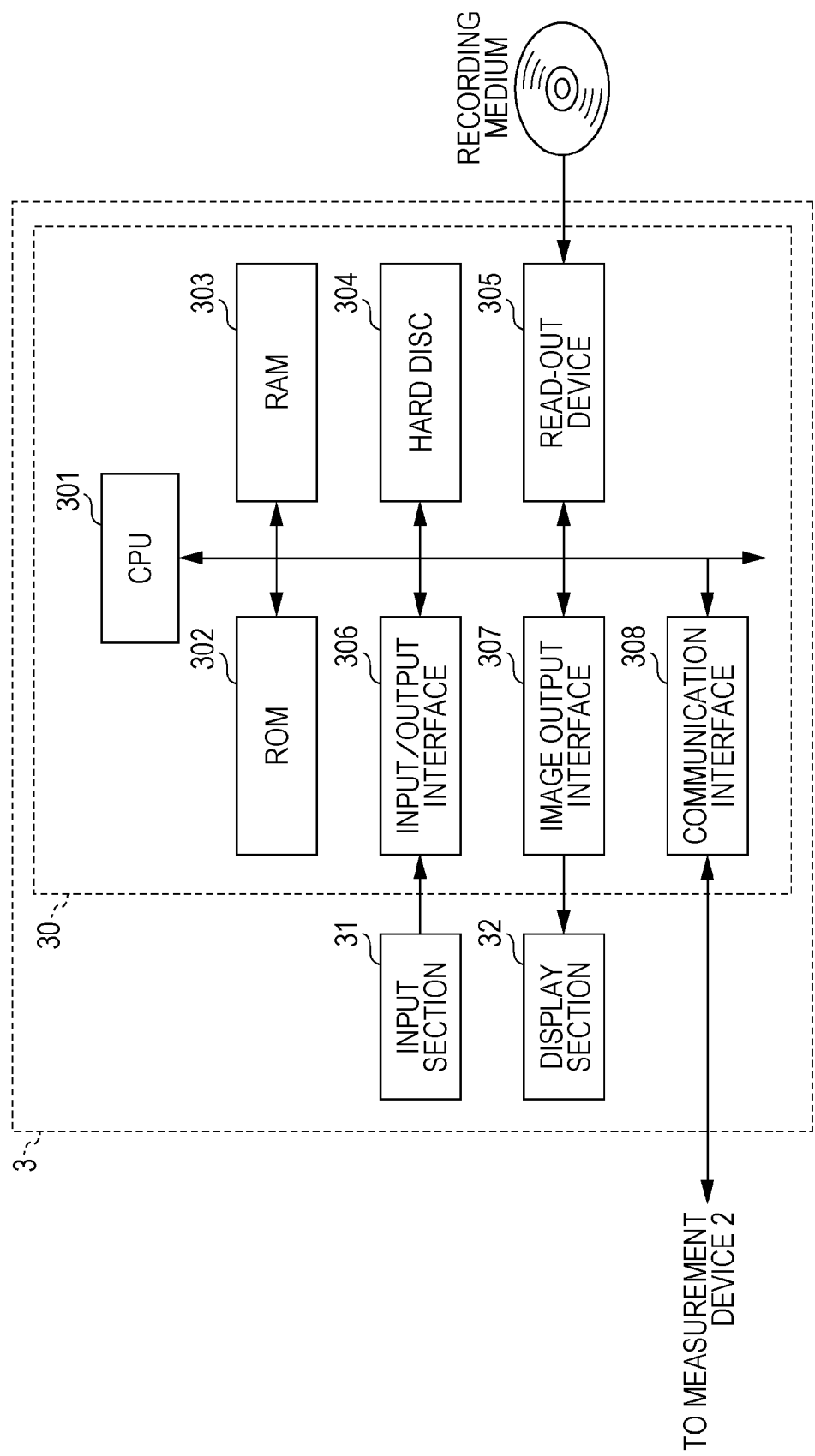
FIG. 5 is a diagram showing a configuration of a data processing device according to the embodiment.

As shown in FIG. 5, the data processing device 3 includes a personal computer, and is configured by a main body 30, the input section 31, and the display section 32. The main body 30 includes a CPU 301, a ROM 302, a RAM 303, a hard disc 304, a read-out device 305, an input/output interface 306, an image output interface 307, and a communication interface 308.

The CPU 301 executes a computer program stored in the ROM 302 and a computer program loaded in the RAM 303. The RAM 303 is used to read out the computer program recorded on the ROM 302 and a computer program recorded on the hard disc 304. The RAM 303 is also used as a workspace of the CPU 301 when executing the computer programs.

The hard disc 304 is installed with various computer programs to be executed by the CPU 301 such as an operating system and an application program, as well as data used in executing the computer programs. Specifically, the hard disc 304 is installed with a program and the like for analyzing the measurement result transmitted from the measurement device 2 to be displayed on the display section 32 based on the generated analysis result.

The CPU 301 acquires feature parameters such as the forward scattered light intensity, the side fluorescence intensity, and the like based on each signal FSC, SSC, SFL, and creates frequency distribution data for analyzing the cells and the nuclei based on such feature parameters by executing the program installed in the hard disc 304. The CPU 301 then performs discrimination processing of the particles in the measurement specimen based on the frequency distribution data, and determines whether or not the cell to be measured (epidermal cell) is abnormal, specifically, whether or not the cell is the cancerous cell (atypical cell). Such a determination made by the CPU 301 will be described later with reference to FIG. 9.

The read-out device 305 is configured by a CD drive, a DVD drive, or the like, and can read out computer programs and data recorded on a recording medium. The input section 31 including a keyboard and the like is connected to the input/output interface 306, so that instructions and data are input to the data processing device 3 when the operator uses the input section 31. The image output interface 307 is connected to the display section 32 configured by a display and the like, and outputs a video signal corresponding to the image data to the display section 32.

The display section 32 displays the image based on the input video signal. The display section 32 displays various types of program screens. The communication interface 308 enables transmission and reception of data respect to the measurement device 2.

As shown in FIG. 4, the operation control of the main detecting section 22 and the signal processing section 24 of the measurement device 2 is executed by the microprocessor 251 of the measurement control section 25. The operation control of the sub-detecting section 13, the signal processing section 27, and the preparation device section 29 of the measurement device 2 is executed by the microprocessor 281 of the preparation control section 28. The control of the data processing device 3 is executed by the CPU 301.

In the analysis by the canceration information providing device 1, the specimen container 4 accommodating the biological specimen and the preservation solution, of which a main component is methanol, is set in the sample setting section 2a (see FIG. 2) by the operator, and then the analysis by the canceration information providing device 1 starts.

When the measurement starts, the dispersion treatment (first dispersion treatment) of the aggregated cells in the specimen is carried out by the first dispersion section 12 (S11). Specifically, the specimen in the specimen container 4 set in the sample setting section 2a is aspirated by the sample pipette section 11 and supplied into the specimen accommodating unit 12a. The specimen supplied to the specimen accommodating unit 12a is dispersed by the first dispersion section 12.

After the first dispersion treatment is finished, the dispersed specimen is supplied to the specimen retrieving unit 13a of the sub-detecting section 13 by the sample pipette section 11, and the dispersed specimen is flowed to the flow cell of the sub-detecting section 13 similar to the flow cell 43 of FIG. 3A by a predetermined amount. In the sub-detecting section 13, the detection (pre-measurement) of the number of normal cells existing on the surface layer side at least than the basal cells in the epithelial tissue contained in the specimen is carried out by a flow cytometry technique (S12). In the present embodiment, the number of surface layer cells and intermediate layer cells is detected as the number of normal cells. The concentration of the specimen is calculated by the number of cells including the surface layer cells and the intermediate layer cells obtained by the pre-measurement and the volume of the specimen supplied to the sub-detecting section 13.

Then, the aspiration amount of the specimen for preparing the measurement specimen to use in the actual measurement is determined by the microprocessor 281 based on the calculated concentration (S13). In other words, the liquid measure of the specimen necessary for carrying out the actual measurement is computed to the extent that the number of cells including the surface layer cells and the intermediate layer cells is ensured based on the concentration (number of cells per unit volume) of the specimen used in the pre-measurement, and the number of cells including the surface layer cells and the intermediate layer cells necessary for the cancer cell detection in the actual measurement. In the present embodiment, the number of surface layer cells and intermediate layer cells to supply to the flow cell 43 of the main detecting section 22 is assumed to be about twenty thousand. In this case, the specimen to supply to the discriminating/replacing section 14 needs to contain about a hundred thousand surface layer cells and intermediate layer cells. Thus, the liquid measure of the specimen in S13 is computed so that about a hundred thousand surface layer cells and intermediate layer cells are supplied to the discriminating/replacing section 14.

In the number of cells including the surface layer cells and the intermediate layer cells obtained in the pre-measurement, the single cells and the aggregated cells of the epidermal cells coexist, and furthermore, white blood cells and the like other than the epidermal cells are also contained. In other words, even when a hundred thousand surface layer cells and intermediate layer cells are supplied to the discriminating/replacing section 14 as described above, the cells supplied to the flow cell 43 of the main detecting section 22 are actually around twenty thousand, which is the target number. However, on the basis of the number of cells obtained in the pre-measurement, the number of cells necessary in the actual measurement can be maintained constant to a certain extent.

The discriminating/replacing treatment is then performed for the specimen of the computed liquid measure (S14). In other words, the sample pipette section 11 is driven by the preparation control section 28, and the specimen having undergone the first dispersion treatment is aspirated by the computed liquid measure from the specimen accommodating unit 12a of the first dispersion section 12. The aspirated specimen is supplied to the discriminating/replacing section 14, whereby the discriminating/replacing treatment starts.

The dispersion treatment (second dispersion treatment) of the aggregated cells in the specimen is then carried out by the second dispersion section 16 (S15). Specifically, the container transfer section 15 grips and takes out the measurement specimen container 5 in the holder 18b of the reaction section 18, and positions the same in the specimen exchanging section 11b. The specimen aspirated by the sample pipette section 11 from the discriminating/replacing section 14 is then supplied to the measurement specimen container 5 positioned in the specimen exchanging section 11b. Thereafter, the measurement specimen container 5 is transferred to the second dispersion section 16 by the container transfer section 15, and the second dispersion treatment is performed.

After the measurement specimen container 5 containing the specimen having undergone the second dispersion treatment is set in the holder 18b of the reaction section 18, the reagent (RNase) is added by the first reagent adding section 19 and warmed by the reaction section 18, whereby the RNA removal processing of the cells to be measured in the measurement specimen container 5 is carried out (S16). After the RNA removal processing, the reagent (stain solution) is added by the second reagent adding section 20 and warmed by the reaction section 18, whereby the DNA stain treatment of the cells to be measured in the measurement specimen container 5 is carried out (S17). In the present embodiment, since the significant number of cells necessary for the actual measurement is maintained constant to a certain extent by the pre-measurement, the extent of staining when staining the cells is less likely to vary for each measurement.

The measurement specimen having undergone the DNA stain treatment is then aspirated by the specimen aspirating section 21. The aspirated measurement specimen is fed to the flow cell 43 (see FIG. 3A) of the main detecting section 22, and the actual measurement on the cells in the measurement specimen is carried out (S18).

After the actual measurement, the obtained measurement data is transmitted from the measurement control section 25 of the measurement device 2 to the data processing device 3 (S19). Specifically, the forward scattered light signal (FSC), the side scattered light signal (SSC), and the side fluorescence signal (SFL) obtained for each cell in the measurement specimen are transmitted to the data processing device 3. The CPU 301 of the data processing device 3 constantly determines whether or not the measurement data is received from the measurement device 2. When receiving the measurement data from the measurement device 2, the CPU 301 of the data processing device 3 performs analysis processing based on the measurement data (S20). The details of the analysis processing of S20 will be described later with reference to FIG. 9.

A procedure for acquiring the canceration information in the present embodiment will now be described.

Figure 6:
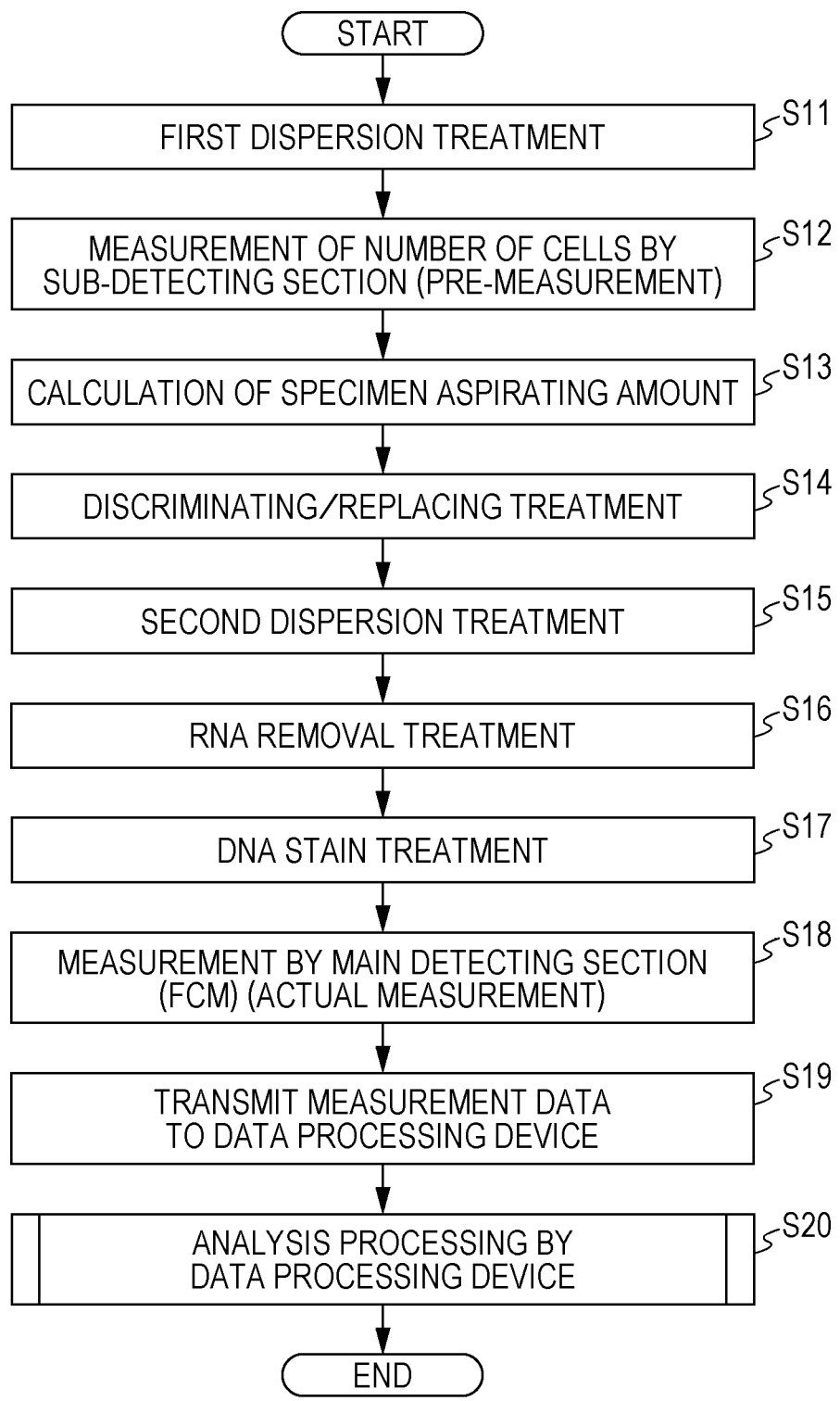
FIG. 6 is a flowchart showing an analyzing operation of the canceration information providing device according to the embodiment.
Figure 7A:
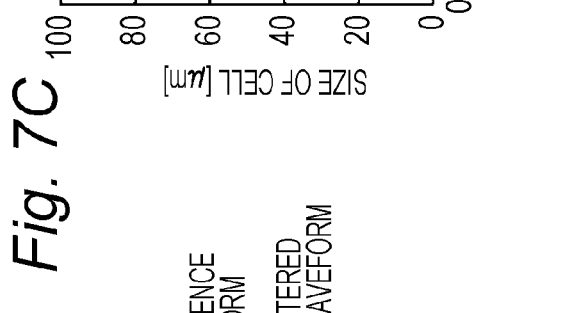
FIG. 7A is a view describing a forward scattered light signal and a side fluorescence signal in the embodiment.

FIG. 7A is a view describing the forward scattered light signal (FSC) and the side fluorescence signal (SFL) obtained in the actual measurement (S18 of FIG. 6). FIG. 7A shows a schematic diagram of the cell including the cell nucleus, and the waveform of the forward scattered light signal and the waveform of the side fluorescence signal obtained from the relevant cell. The vertical axis represents the intensity of light. The width of the waveform of the forward scattered light intensity represents a numerical value (size C of cell) indicating the width of the cell, and the width of the waveform of the side fluorescence light intensity represents a numerical value (size N of cell nucleus) indicating the width of the cell nucleus. As shown with dashed lines, the area of a region determined by the waveform of the side fluorescence intensity and a predetermined baseline represents the DNA amount of the cell.

Figure 7C:
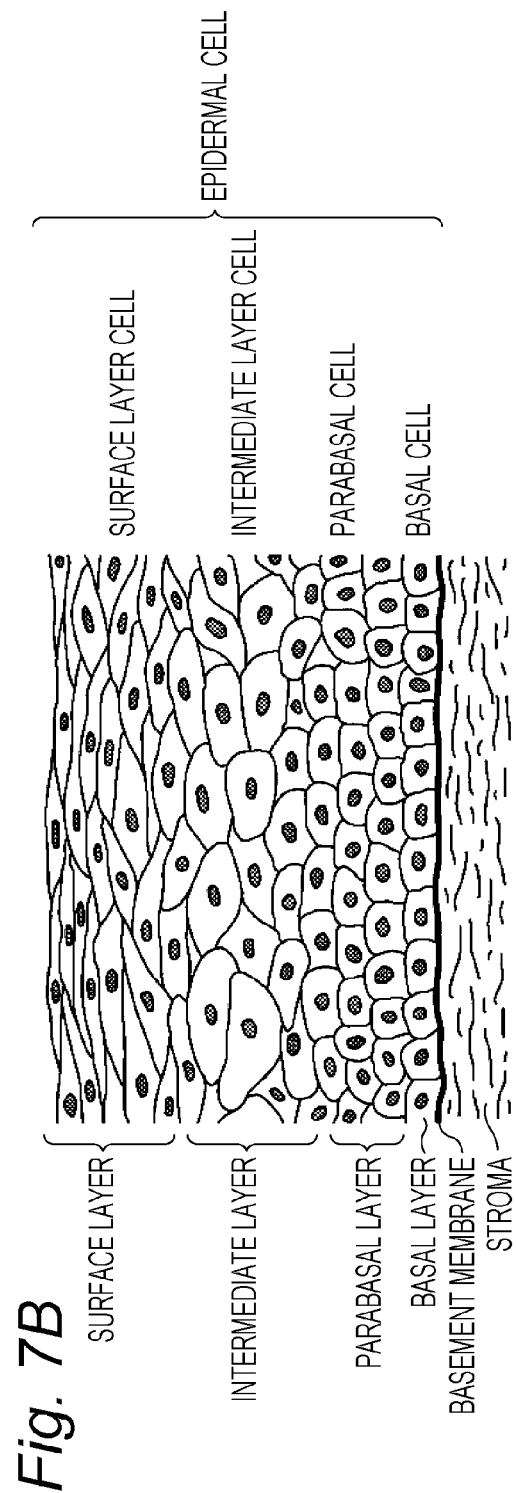
FIG. 7C is a graph showing a relationship between the N/C ratio and the size of the cell.
Figure 7B:
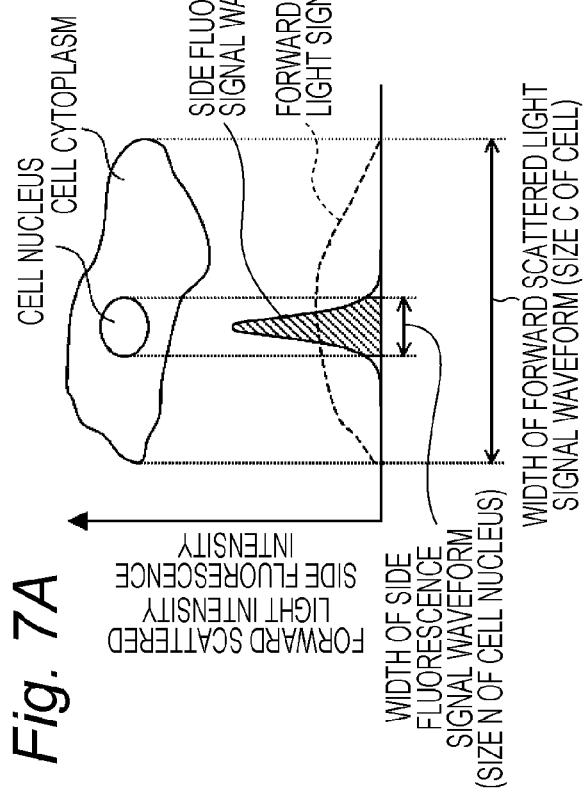
FIG. 7B is a view schematically showing an enlarged cross-section of epidermal cells of a uterine cervix.

FIG. 7B is a view schematically showing an enlarged cross-section of the epidermal cells of the uterine cervix. As shown in FIG. 7B, a layer (basal layer) formed by basal cells, a layer (parabasal layer) formed by parabasal cells, a layer (intermediate layer) formed by intermediate layer cells, and a layer (surface layer) formed by surface layer cells are formed in order from the basement membrane in the uterine cervix. The basal cells near the basement membrane are differentiated into the parabasal cells, the parabasal cells are differentiated into the intermediate layer cells, and the intermediate layer cells are differentiated into the surface layer cells.

The cells associated with the canceration among the epidermal cells are basal cells in the epidermal cells of the uterine cervix. In the process of becoming cancer, the basal cell acquires dysplasia and becomes the atypical cell. The atypical cell acquires the growth ability, and occupies from the basal layer side to the surface layer side. Thus, in the initial stage of cancer, a great amount of neoplastic cells exist in the cells existing in the basal layer, the parabasal layer, and the intermediate layer in the epidermal cells of the uterine cervix. On the contrary, in the initial stage of cancer, the neoplastic cells are very few in the cells existing on the surface layer side of the epidermal cells of the uterine cervix.

In the epidermal cells, the size of the cell gradually becomes smaller but the size of the cell nucleus gradually becomes greater from the layer on the surface layer side toward the layer on the basement membrane side. Therefore, the ratio (hereinafter referred to as "N/C ratio") of the size (N) of the cell nucleus with respect to the size (C) of the cell also gradually becomes greater from the layer on the surface layer side toward the layer on the basement membrane side. Thus, the N/C ratio and the size C of the cell have the relationship shown in FIG. 7C, for example. The parabasal cells and the basal cells can be extracted by extracting the cells having a large N/C ratio.

The epidermal cells of the uterine cervix that can be harvested from the subject are the parabasal cells, the intermediate layer cells, and the surface layer cells, and the precancerous lesion appears in an early stage on the basal cell side as described above. Thus, if the parabasal cells are appropriately harvested when harvesting the epidermal cells from the subject, the precancerous lesion of the initial stage of cancer can be appropriately detected in the determination of canceration, to be described later.

In the present embodiment, whether or not the parabasal cells are appropriately harvested (appropriateness of harvesting of parabasal cells) is determined before the determination of canceration. In determining the appropriateness of harvesting of parabasal cells, determinations 1, 2 focusing on the N/C ratio are used.

In determination 1, the number of cells N1 of the parabasal cells in which the canceration is assumed to easily progress is acquired by extracting the cell having a large N/C ratio. In determination 1, a determination is made that the harvesting of parabasal cells is inappropriate when the number of cells N1 is few.

In determination 2, the number of cells N2 of the cells existing closer to the surface layer side than the parabasal cells and in which canceration is less likely to progress compared to the parabasal cells is acquired by extracting the cell having a small N/C ratio. In determination 2, when the number of cells N2 is few and a value obtained by dividing the number of cells N1 by the number of cells N2 is small, a determination is made that the harvesting of parabasal cells is inappropriate. In other words, when the number of cells N2 is few, the absolute number of the cells at the time of harvesting is sometimes few, and thus the possibility that the harvesting of parabasal cells is inappropriate is assumed to be high. Furthermore, when the value obtained by dividing the number of cells N1 by the number of cells N2 is small, the parabasal cells is sometimes few compared to the cells existing closer to the surface layer side than the parabasal cells, and thus the harvesting of parabasal cells is assumed to be inappropriate.

Figure 8A:
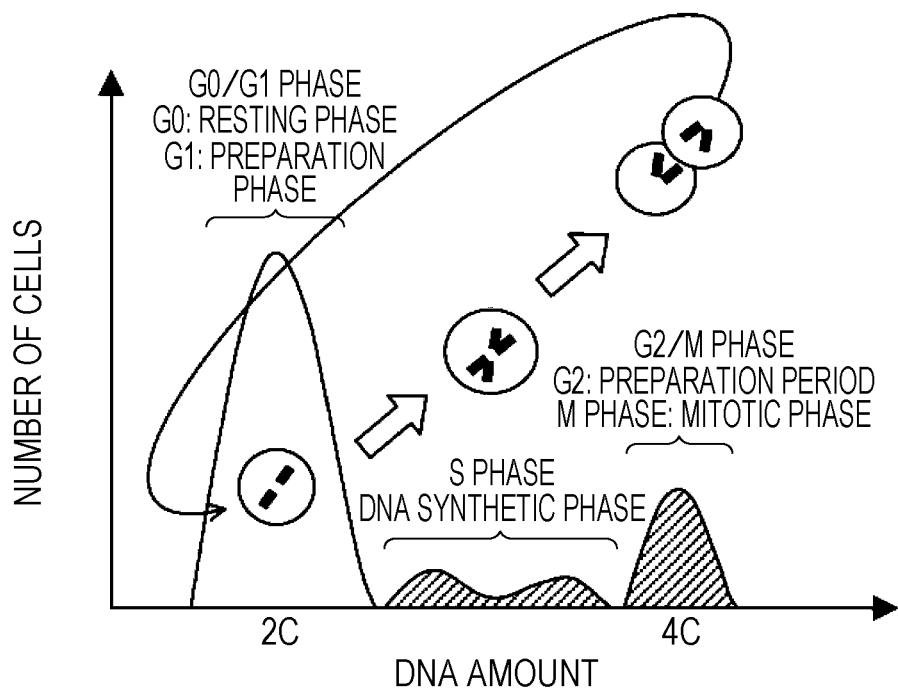
FIG. 8A is a graph showing a relationship between the DNA amount and the number of cells in a cell cycle according to the embodiment and FIG. 8B is a graph showing the DNA amount that changes for every cell cycle.

FIG. 8A is a graph showing a relationship between the DNA amount and the number of cells in the cell cycle. As shown in FIG. 8A, the cell becomes two cells through events such as DNA replication, chromosomal division, nuclear division, and cytoplasmic division according to the constant cycle (cell cycle), and the cells return to the starting point. The cell cycle can be divided into four phases of G1 phase (period of preparation and inspection to enter S phase), S phase (DNA synthetic phase), G2 phase (period of preparation and inspection to enter M phase), and M phase (mitotic phase) according to the stages, and the cell cycle also includes a G0 phase (resting phase) in which the growing of the cells is in pause in addition to the four phases, and accordingly the cell is in one of the stages of the five phases.

Figure 8B:
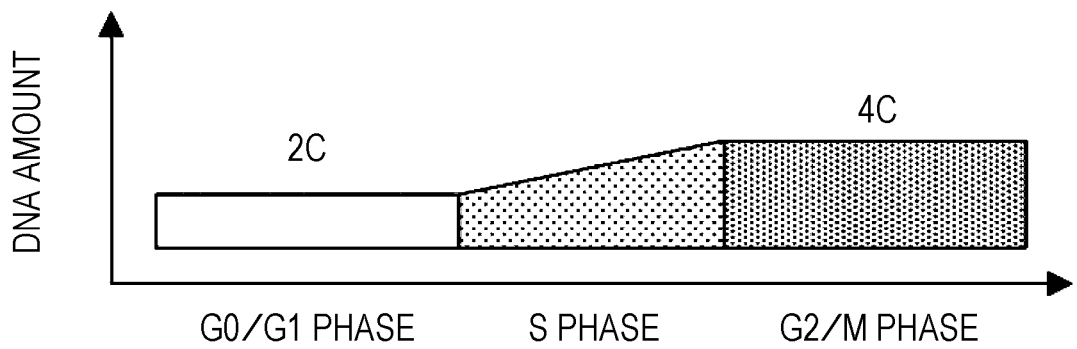

When the cell grows according to the cell cycle, the chromosomes of the nucleus in the cell also increase, and thus which state of the cell cycle the cell is in can be estimated by measuring the DNA amount of the cell. In the case of the normal cell, as shown in FIG. 8B, the DNA amount in the G0/G1 phase is a constant value (2C), and the DNA amount gradually increases in the following S phase and thereafter becomes a constant value (4C) after entered the G2 phase, which value is also maintained in the M phase. C represents the genomic DNA amount per haploid. In other words, 2C represents the DNA amount of two times the genomic DNA content per haploid, and 4C represents the DNA amount of four times the genomic DNA content per haploid. The DNA amount of the normal cell in the G0 phase or the G1 phase of the cell cycle is 2C. A histogram shown in FIG. 8A is obtained when the histogram of the DNA amount is created for the normal cell. A hill having the highest peak corresponds to the cell in the G0/G1 phase in which the DNA amount is the least, a hill having the next highest peak corresponds to the cell in the G2/M phase in which the DNA amount is the greatest, and a hill in between corresponds to the cell in the S phase.

In the case of normal cells, the number of cells in the state of S phase and the G2/M phase are extremely small compared to the number of cells in the G0/G1 phase. However, in the case of neoplastic cells, the number of cells in the state of S phase and the G2/M phase is greater compared to the normal cells. Furthermore, in the case of neoplastic cells, the DNA amount also increases since the number of chromosomes in the cell also increases.

In the present embodiment, the determination method focusing on the N/C ratio and the DNA amount is used in the determination of canceration.

Specifically, the parabasal cells in which canceration is assumed to easily progress are extracted by extracting the cells having a large N/C ratio. The cells having a large DNA amount and the cells having a small DNA amount are then extracted among the cell group extracted in such a manner, so that the cells (first cell) having a high possibility of being neoplastic cells and the cells (second cell) having a low possibility of being neoplastic cells are effectively extracted. Generally, when the canceration of the tissue advances, the number of first cells increases and the number of second cells decreases. Thus, the ratio between the numbers of both cells greatly differs between when the tissue is normal and when the tissue is cancerous. The determination of canceration is carried out based on such a ratio. Thus, when the ratio between the two numbers of cells in which the increasing/decreasing tendency is opposite to each other is used, the determination result of high reliability can be obtained even if the cell to be measured contained in the measurement specimen is relatively few.

Figure 10A:
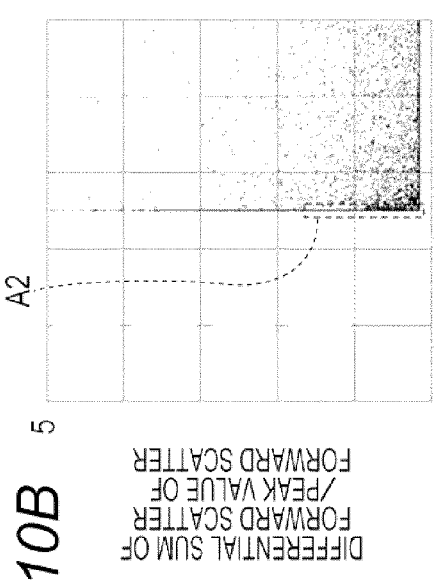
FIGS. 10A to 10C are graphs showing scattergrams and FIG. 10D is a graph showing a histogram, each generated by the analysis processing according to the embodiment.

In the analysis processing in the data processing device 3 shown in FIG. 9, the CPU 301 of the data processing device 3 first creates a scattergram shown in FIG. 10A when receiving the measurement data from the measurement device 2. In FIG. 10A, the horizontal axis represents the size of the cell (width of forward scattered light signal waveform), and the vertical axis represents the DNA amount (sum of side fluorescence signal waveform). The CPU 301 then separates the white blood cells and the epidermal cells (S101). Specifically, the CPU 301 sets a region A1 in which a lower left region corresponding to the white blood cells is taken away from the entire region in the scattergram of FIG. 10A, and extracts the cells contained in the region A1.

Figure 10B:
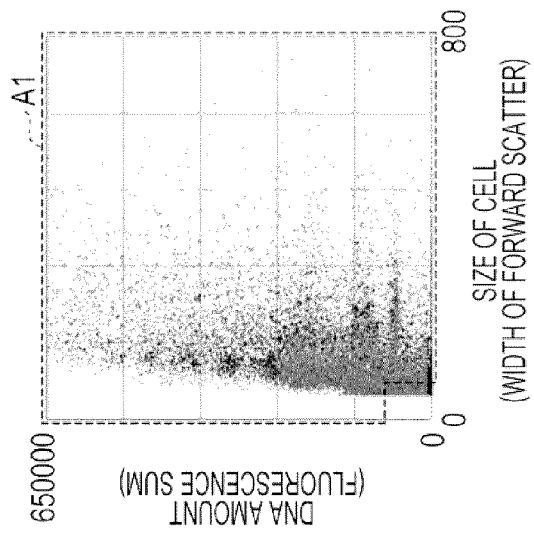

The CPU 301 then creates a scattergram shown in FIG. 10B from the cell group extracted in S101. In FIG. 10B, the horizontal axis represents (differential sum of side fluorescence signal/peak value of side fluorescence signal), and the vertical axis represents (differential sum of forward scattered light signal/peak value of forward scattered light signal). The CPU 301 then separates the single epidermal cells and the aggregated epidermal cells (S102). Specifically, the CPU 301 sets a region A2 corresponding to the single epidermal cells in the scattergram of FIG. 10B, and extracts the cells contained in the region A2. The aggregated cells are removed to suppress the lowering in the accuracy of the determination on the appropriateness of cell harvesting, to be described later, and the determination of canceration.

Figure 10C:
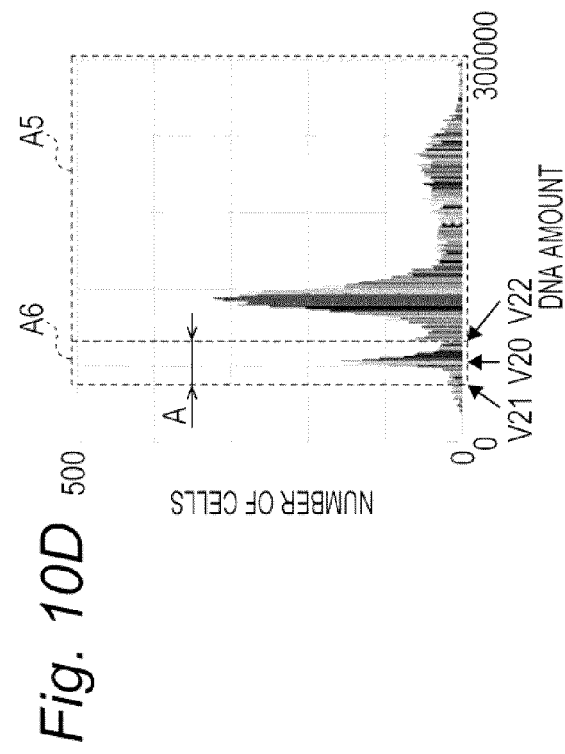

The CPU 301 then creates a scattergram shown in FIG. 10C from the cell group extracted in S102 (S103). In the scattergram of FIG. 10C, the horizontal axis represents a value (N/C ratio) obtained by dividing the size N of the cell nucleus by the size C of the cell, and the vertical axis represents the size of the cell.

The CPU 301 then performs the determination on the appropriateness of cell harvesting (S104 to S106). The determination on the appropriateness of cell harvesting includes determination 1 (S104) and determination 2 (S105, S106) described above. If determined as inappropriate in either determination 1 or 2, a determination is made as inappropriate in the determination on the appropriateness of cell harvesting.

The CPU 301 sets a region A3 where V12≤N/C ratio≤V13 is satisfied in the scattergram of FIG. 10C, and determines whether the number of cells N1 contained in the region A3 is smaller than a threshold value s1 (S104).

The value at the left end and the value at the right end of the region A3 are set such that the values of the N/C ratio are V12 and V13, respectively. V12 is the threshold value that divides between the intermediate layer cell and the parabasal cell, and is appropriately set from the standpoints of sensitivity and specificity. In the present embodiment, V12 is set in a range of 0.2 to 0.4. V13 is the threshold value that divides between the parabasal cell, and the basal cell and an unknown cell, and is appropriately set from the standpoints of sensitivity and specificity. In the present embodiment, V13 is set in a range of 0.6 to 1. The threshold value s1 is a threshold value for determining the appropriateness of harvesting of parabasal cells, and is appropriately set from the standpoints of sensitivity and specificity. In the present embodiment, the threshold value s1 is set in a range of 50 to 1000.

Figure 11A:
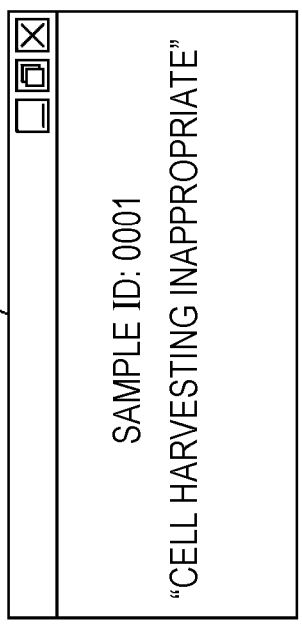
FIGS. 11A to 11D are views showing dialogues displayed on a display section according to the embodiment.

If the number of cells N1 is not sufficient, there is a possibility the harvesting of parabasal cells is inappropriate. Therefore, if the number of cells N1 is smaller than the threshold value s1 (S104: Yes), that is, if the determination of determination 1 shows inappropriateness, the determination on the appropriateness of cell harvesting is also made as inappropriate. The CPU 301 displays a notification that the harvesting of parabasal cells is inappropriate (S107). Specifically, the CPU 301 displays a dialogue D1 showing "inappropriate cell harvesting" on the display section 32, as shown in FIG. 11A. In the dialogue D1, a message such as "low reliability" (FIG. 11D), "NG", "unanalyzable", and the like may be displayed. The CPU 301 terminates the processing without performing the determination of canceration (S108, S109), and the output of canceration information (S110, S111) of post-stages.

If the number of cells N1 is greater than or equal to s1 (S104: NO), the determination of determination 1 is made as appropriate. In this case, the determination by determination 2 is further carried out.

If the number of cells N1 is greater than or equal to the threshold value s1 (S104: NO), the CPU 301 set a region A4 where V11≤N/C ratio≤V12 is satisfied in the scattergram of FIG. 10C and determines whether the number of cells N2 contained in the region A4 is smaller than the threshold value s2 (S105).

The value at the left end and the value at the right end of the region A4 are set such that the values of the N/C ratio are V11 and V12, respectively. V11 is a threshold value provided so that the surface layer cells and the intermediate layer cells are contained in the range of V11≤N/C ratio≤V12, and is appropriately set from the standpoints of sensitivity and specificity. In the present embodiment, V11 is set in a range of smaller than V12 and greater than or equal to 0. The threshold value s2 is a threshold value for determining the appropriateness of harvesting of parabasal cells, and is appropriately set from the standpoints of sensitivity and specificity. In the present embodiment, the threshold value s2 is set in a range of 5000 to 20000. According to the Bethesda system, it is necessary for the liquid processing sample to be considered appropriate to contain at least 5000 or more flat epidermal cells that are well preserved and seen clearly. The threshold value s2 of the present embodiment is thus set in the range of 5000 to 20000 in view of the Bethesda system.

If the number of cells N2 is smaller than the threshold value s2 (S105: YES), the CPU 301 determines whether a value (ratio of number of cells N1 and number of cells N2) obtained by dividing the number of cells N1 obtained in S104 by the number of cells N2 obtained in S105 is smaller than a threshold value s3 (S106).

The threshold value s3 is a threshold value for determining whether or not the number of parabasal cells is large compared to the cells closer to the surface layer side than the parabasal cells, and is appropriately set from the standpoints of sensitivity and specificity. In the present embodiment, the threshold value s3 is set in a range of 0.1 to 0.4.

If the number of cells N2 is smaller than the threshold value s2 (S105: YES) and the ratio of the number of cells N1 with respect to the number of cells N2 is smaller than the threshold value s3 (S106: YES), the determination of determination 2 is made as inappropriate. Thus, the determination on the appropriateness of cell harvesting is also made as inappropriate, and the CPU 301 displays a notification that the harvesting of parabasal cells is inappropriate (S107).

If the number of cells N2 is greater than or equal to s2 (S105: NO) or the ratio of the number of cells N1 with respect to the number of cells N2 is greater than or equal to the threshold value s3 (S106: NO), the determination of determination 2 is made as appropriate. Thus, the determination on the appropriateness of cell harvesting is also made as appropriate.

Figure 10D:
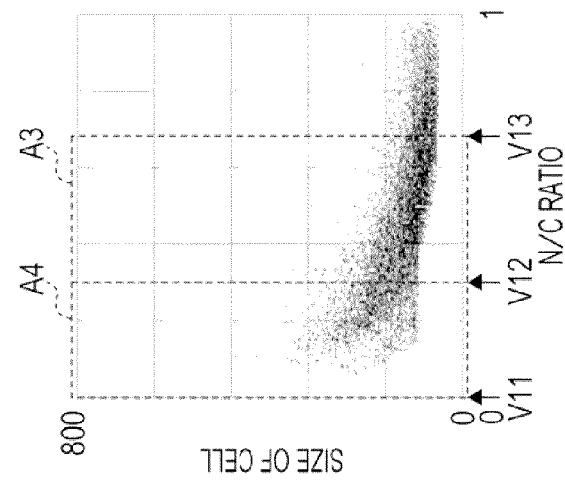

If the determination on the appropriateness of cell harvesting shows appropriateness, the determination of canceration (S108, S109) is carried out. The CPU 301 extracts the cell group satisfying V12≤N/C ratio≤V13 (cell group contained in region A3) in the scattergram of FIG. 10C, and creates a histogram (DNA ploidy) shown in FIG. 10D (S108). In the histogram of FIG. 10D, the horizontal axis represents the DNA amount and the vertical axis represents the number of cells.

The CPU 301 then acquires the number of cells in which the DNA amount is greater than or equal to that of the normal cells in the S phase, that is, the number of cells having a DNA amount exceeding the DNA amount of the normal cells in which the cell cycle is in the G0 phase or the G1 phase in the histogram of FIG. 10D. Specifically, the CPU 301 sets a region A5 in the histogram of FIG. 10D, and acquires number of cells N3 contained in the region A5. The CPU 301 also acquires the number of cells in which the DNA amount is 2C of the normal cells, that is, the number of cells having a DNA amount of the normal cells in which the cell cycle is in the G0 phase or the G1 phase. Specifically, the CPU 301 sets a region A6 in the histogram of FIG. 10D, and acquires the number of cells N4 contained in the region A6.

The value at the left end of the region A5 is set to correspond to the upper limit value of the range of DNA amount detected as the DNA amount of the normal cells in which the cell cycle is in the G0/G1 phase in the canceration information providing device 1, and the right end of the region A5 is set to include all the cells in the right.

The value at the right end of the region A6 is set as a value dividing between the DNA amount (2C) of the normal cell in the G0 phase or the G1 phase and the DNA amount of the normal cell in the S phase. Specifically, the value V20 indicating the DNA amount of the normal cell in which the cell cycle is in the G0 phase or G1 phase is set, where V21 and V22 are set such that V20 is included in the range between V21 and V22 and the width of the range between V21 and V22 is A. In the present embodiment, the region A5 and the region A6 are set so as to be adjacent at the value V22.

The CPU 301 then acquires a value (ratio of number of cells N3 and number of cells N4) obtained by dividing the number of cells N3 in which the DNA amount is greater than or equal to that of the normal cell in the S phase by the number of cells N4 in which the DNA amount is 2C. The CPU 301 then determines whether the ratio between the number of cells N3 and the number of cells N4 is greater than or equal to a predetermined threshold value s4 (S109). The determination of canceration indicates positive if the ratio between the number of cells N3 and the number of cells N4 is greater than or equal to the threshold value s4 (S109: YES), and the determination of canceration indicates negative if the ratio between the number of cells N3 and the number of cells N4 is smaller than the threshold value s4 (S109: NO). The threshold value s4 is a threshold value that divides between the cancer sample and the negative sample, and is appropriately set from the standpoints of sensitivity and specificity.

Figure 11B:
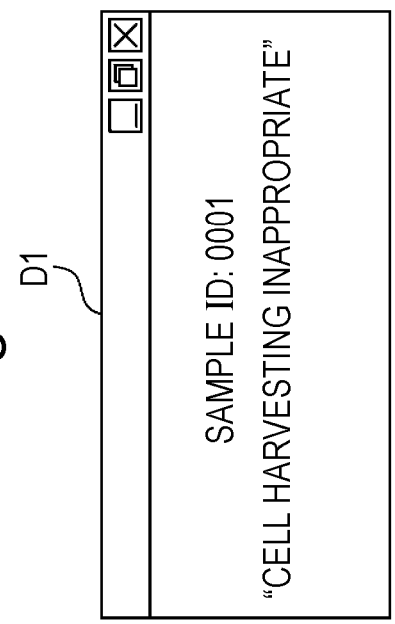
Figure 11C:
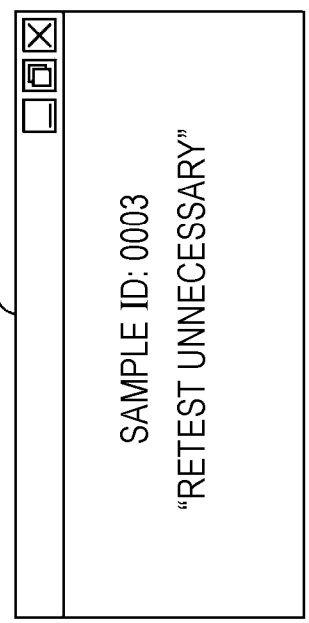
Figure 11D:

When the determination of canceration indicates positive, the CPU 301 displays a notification that a retest is necessary as information related to canceration (S110). Specifically, the CPU 301 displays a dialogue D2 showing "retest necessary" on the display section 32, as shown in FIG. 11B. When the determination of canceration indicates negative, the CPU 301 displays a notification that the retest is unnecessary (S111). Specifically, the CPU 301 displays a dialogue D3 showing "retest unnecessary" on the display section 32, as shown in FIG. 11C.

The determination on the appropriateness of cell harvesting of the present embodiment and the determination on the appropriateness (LBC appropriateness determination) of cell harvesting carried out in cytological diagnosis will now be described.

FIGS. 12A to 12F are graphs showing scattergrams created in S103 based on six samples each having sample IDs 1 to 6. FIGS. 13A to 13F are images (LBC images) showing slides created in the liquid based cytology (LBC) based on the six samples each having sample IDs 1 to 6.

FIGS. 14A to 14F are tables showing simulation results performed on the six samples each having sample IDs 1 to 6. In each table, the result of the determination on the appropriateness of cell harvesting of the present embodiment, and the result of the LBC appropriateness determination based on the Bethesda system are shown. In the simulation, the threshold value s1 is set to be greater than 227 and smaller than or equal to 863, the threshold value s2 is set to be greater than or equal to 5000 and smaller than or equal to 13768, and the threshold value s3 is set to between 0.1 and 0.4.

In each of the samples having sample IDs 1 to 3, since the determinations 1, 2 are appropriate as shown in the item of the determination result, the determination on the appropriateness of cell harvesting is also made as appropriate as shown in the item of the overall determination. In each of the samples having sample IDs 1 to 3, the LBC appropriateness determination is also appropriate. In each of the samples having sample IDs 4 to 6, determination 2 shows appropriateness but determination 1 shows inappropriateness, and thus the determination on the appropriateness of cell harvesting is made as inappropriate. In each of the samples having sample IDs 4 to 6, the LBC appropriateness determination is also inappropriate.

Therefore, the result of the determination on the appropriateness of cell harvesting in the present embodiment is similar to the result of the determination on the appropriateness of cell harvesting in cytological diagnosis. Thus, the accuracy in the determination of appropriateness of cell harvesting according to the present embodiment may be assumed to be satisfactory.

In the present embodiment, the appropriateness of cell harvesting of parabasal cells, which are cells useful in the determination of canceration, is determined. Thus, the precancerous lesion can be detected and the possibility of cancer can be appropriately determined, whereby the accuracy in the determination of canceration can be enhanced and the treatment for cancer can be started at an early stage.

In the present embodiment, when determined as inappropriate in the determination on the appropriateness of cell harvesting of FIG. 9, the dialogue D1 indicating that the harvesting of parabasal cells is inappropriate is displayed on the display section 32. The operator then can visually grasp that the parabasal cell is not appropriately harvested.

In the present embodiment, the first dispersion treatment is carried out in S11 of FIG. 6, and the second dispersion treatment is carried out in S15 of FIG. 6. Thus, even if the cells harvested from the epithelial tissue are aggregated, the aggregated cells contained in the measurement specimen are dispersed, and thus the appropriateness of the cell harvesting of parabasal cells can be determined. The white blood cells and the epidermal cells (single epidermal cells, aggregated epidermal cells) are separated in S101 of FIG. 9, and the signal epidermal cells and the aggregated epidermal cells are separated in S102 of FIG. 9. The accuracy in the determination of canceration of the epidermal cell to be measured thus can be enhanced.

In the present embodiment, a certain number of cells necessary for the measurement can be ensured since the pre-measurement is carried out in S12 of FIG. 6.

In the present embodiment, the white blood cells and the epidermal cells (single epidermal cells, aggregated epidermal cells) are separated in S101 of FIG. 9, and the signal epidermal cells and the aggregated epidermal cells are separated in S102 of FIG. 9. Thus, the accuracy in the determination on the appropriateness of cell harvesting is suppressed from lowering by the aggregated cells. For example, an undesirable plot by the aggregated epidermal cells is suppressed from being included on the scattergram shown in FIG. 10C. The lowering in the accuracy of the determination on the appropriateness of cell harvesting is thereby suppressed.

In the present embodiment, whether or not the cells are appropriately harvested can be determined based on N1 corresponding to the number of parabasal cells that are useful in the determination of the precancerous lesion in determination 1 (S104) of FIG. 9, whereby the possibility of cancer can be appropriately determined.

In the present embodiment, whether or not the cells are appropriately harvested can be determined based on the number of cells N1/the number of cells N2 corresponding to the ratio indicating the degree of the parabasal cells contained in the harvested cells in S106 of determination 2 of FIG. 9, whereby the appropriateness of cell harvesting of parabasal cells can be determined.

In the present embodiment, whether or not the cells are appropriately harvested is determined based on N2 corresponding to the number of cells existing closer to the surface layer side than the parabasal cells in S105 of determination 2 of FIG. 9, whereby whether the absolute number of cells at the time of harvesting is small can be known. The appropriateness of cell harvesting of parabasal cells thus can be determined.

In the present embodiment, the appropriateness of cell harvesting is determined by determinations 1, 2 shown in FIG. 9, and the appropriateness of cell harvesting is ultimately determined based on the determination results of determinations 1, 2. Whether or not the parabasal cells are appropriately harvested then can be determined. The results of the determination on the appropriateness of cell harvesting shown in FIG. 9 are similar to the determination results on the appropriateness of cell harvesting in the cytological diagnosis, as shown in FIGS. 14A to 14F. Thus, according to determinations 1, 2, results similar to those of the determination on the appropriateness of cell harvesting in cytological diagnosis conventionally carried out can be obtained, so that whether or not the parabasal cells are appropriately harvested can be known without going through the trouble of observing the slide, and the like.

In the present embodiment, when determined as appropriate in the determination on the appropriateness of cell harvesting of FIG. 9, the determination of canceration and the output of canceration information are performed. The canceration information to be output thus has high accuracy.

In the present embodiment, when determined as inappropriate in the determination on the appropriateness of cell harvesting of FIG. 9, the processing is terminated without performing the determination of canceration and the output of canceration information. Thus, if the determination of canceration cannot be appropriately carried out since the harvesting of parabasal cells is inappropriate, the determination of canceration is not performed and hence the diagnosis can be smoothly made. Furthermore, since the output of canceration information is not performed, the information of low reliability can be prevented from being output in advance.

The embodiment of the present invention has been described above, but the present invention is not limited to the embodiment described above, and various modifications other than the above may be made on the embodiment of the present invention.

Figure 15C:
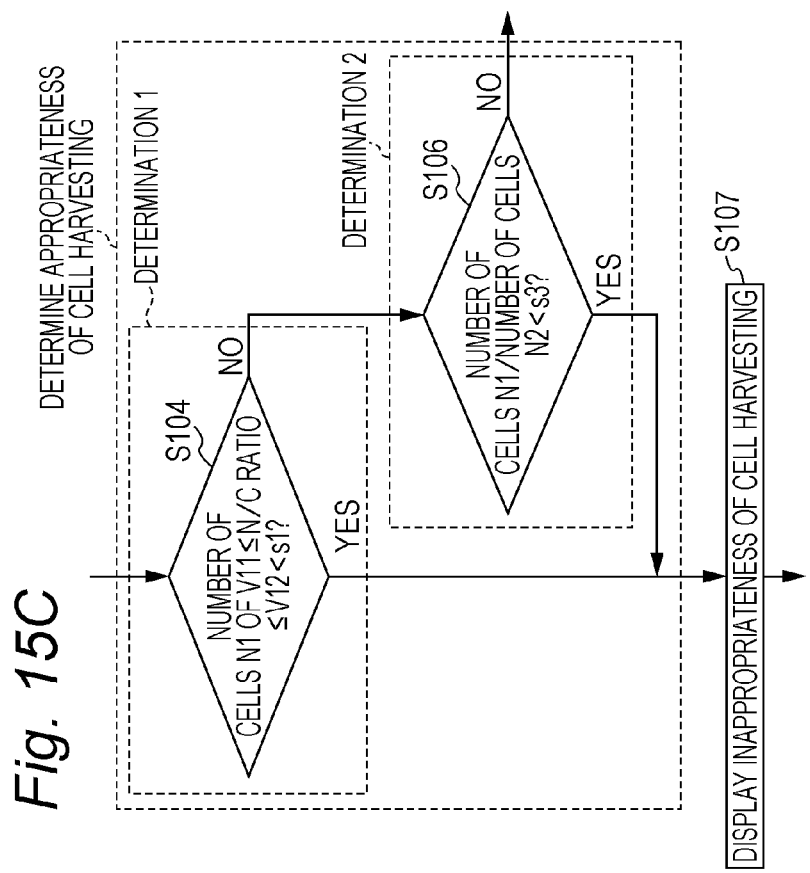
FIGS. 15A 15C are flowcharts showing the determination on the appropriateness of cell harvesting according to modifications.
Figure 15A:
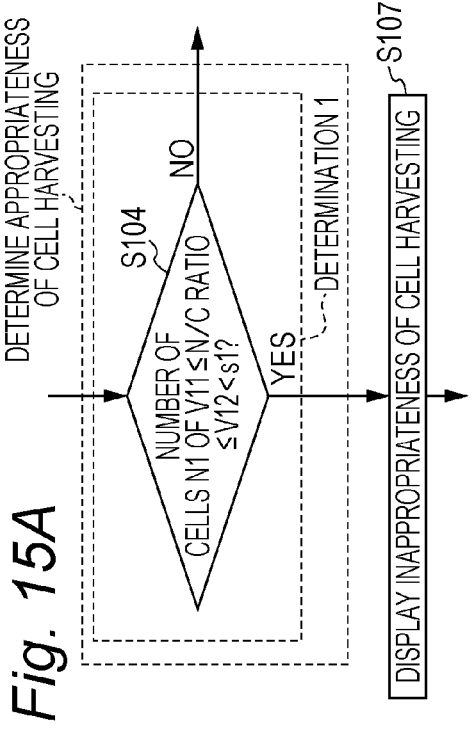
Figure 15B:
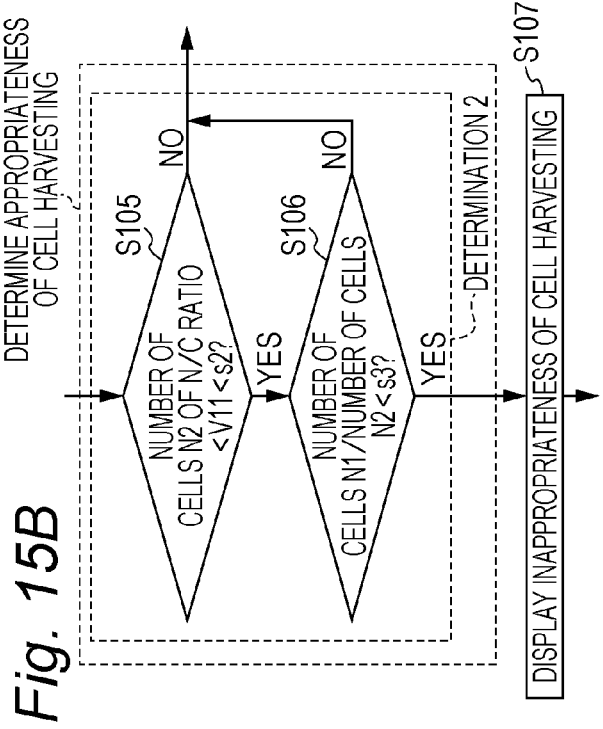

For example, in the embodiment described above, the determination on the appropriateness of cell harvesting of FIG. 9 is configured by determinations 1, 2, but may be configured by only determination 1 as shown in FIG. 15A or may be configured by only determination 2 as shown in FIG. 15B. Furthermore, S105 may be omitted from the determination on the appropriateness of cell harvesting of FIG. 9, and the determination on the appropriateness of cell harvesting may be configured as shown in FIG. 15C.

In the embodiment described above, validation examples showing the effectiveness in the determination on the appropriateness of cell harvesting according to the embodiment described above are shown in FIGS. 14A to 14F. However, an event where a determination is made as inappropriate in determination 2 does not exist in FIGS. 14A to 14F, and hence the effectiveness in determining the sample in which the cell harvesting is inappropriate by determination 2 is not directly shown in the validation examples.

Hereinafter, the effectiveness of determining the sample in which the cell harvesting is inappropriate by determination 2 and excluding the same from the target of determination of canceration will be shown using validation examples.

First, the validation example comparing the determination result of canceration according to the embodiment described above of when only determination 1 is carried out for the determination on the appropriateness of cell harvesting, and the determination result of canceration obtained by the tissue diagnosis on the same sample is shown.

FIGS. 16A and 16B are tables each showing the determination result (S108, S109 of FIG. 9) of canceration of when the determination on the appropriateness of cell harvesting is carried out by only determination 1 as shown in FIG. 15A, and the determination result of the tissue diagnosis. In FIGS. 16A and 16B, each determination is carried out on 1116 samples. In the determination result by the tissue diagnosis in this case, positive is greater than or equal to CIN2 and negative is smaller than or equal to CIN1 and NILM (state assumed as normal in cytological diagnosis).

As shown in FIG. 16A, the samples shown to be positive and negative in the tissue diagnosis among the 214 samples, in which the determination of canceration has been made as positive according to the determination method of the embodiment described above, are 55, 159, respectively. In other words, 159 samples, in which the determination of canceration has been made as positive according to the determination method of the embodiment described above, are negative in the tissue diagnosis. Furthermore, the samples shown to be negative and positive in the tissue diagnosis among the 830 samples that have been determined to be negative in the determination of canceration according to the determination method of the embodiment described above, are 828, 2, respectively. In other words, two samples, in which the determination of canceration has been made as negative according to the determination method of the embodiment described above, are positive in the tissue diagnosis. The number of samples (number of inappropriate samples) shown to be inappropriate in the determination on the appropriateness of cell harvesting by only determination 1 is 72, and the rate of inappropriate samples is 72/(57+987)=6.9%.

FIG. 16B shows the determination result of FIG. 16A in percent figures.

Since the samples in which the determination of canceration has been made as positive according to the determination method of the embodiment described above is 55 among the 57 samples shown to be positive in the tissue diagnosis, the sensitivity of determination of canceration in this case is $55/57=96.5\%$. Furthermore, since the samples in which the determination of canceration has been made as negative according to the determination method of the embodiment described above is 828 among the 987 samples shown to be negative in the tissue diagnosis, the sensitivity of determination of canceration in this case is $828/987=83.9\%$. The proportion (sort out rate) of the number of samples determined as negative in the tissue diagnosis and determined as negative in the determination of canceration according to the determination method of the embodiment described above occupies in the entire number of samples is $828/(57+987+72)=74.2\%$.

Next, the validation example comparing the determination result of canceration according to the embodiment described above of when both determination 1 and determination 2 are carried out for the determination on the appropriateness of cell harvesting, and the determination result of canceration obtained by the tissue diagnosis on the same sample is shown.

FIGS. 16C and 16D are tables each showing the determination result (S108, S109 of FIG. 9) of canceration of when the determination on the appropriateness of cell harvesting is carried out by both determination 1 and determination 2 as shown in the embodiment described above, and the determination result of the tissue diagnosis. In FIGS. 16C and 16D, each determination is carried out on 1116 samples, similar to those in FIGS. 16A and 16B. In the determination result by the tissue diagnosis in this case as well, positive is greater than or equal to CIN2 and negative is smaller than or equal to CIN1 and NILM (state assumed as normal in cytological diagnosis).

As shown in FIG. 16C, the number of inappropriate samples is 122 when determination 2 is added, and hence the number of inappropriate samples increases by 50 compared to when only determination 1 is carried out. The rate of inappropriate sample thus increases to $122/(53+941)=12.3\%$. When determination 2 is added, the relationship between the determination result of canceration according to the present embodiment and the determination result of canceration according to the tissue diagnosis is as shown in FIG. 16C. The determination result of FIG. 16C is shown in percent figures in FIG. 16D.

Comparing FIG. 16A and FIG. 16C, the number of samples in which a determination of canceration has been made as positive in the tissue diagnosis but negative in the determination method (S108, S109 of FIG. 9) according to the embodiment described above reduced from two to one by adding determination 2 to determination 1. Comparing FIG. 16B and FIG. 16D, the determination sensitivity of canceration is enhanced for positive and negative by adding determination 2 to determination 1. Thus, the determination accuracy of canceration is enhanced by adding determination 2 to determination 1. Therefore, the sample inappropriate for the determination of canceration, that is, the sample in which the cell harvesting is inappropriate from the standpoint of canceration determination is effectively removed from the determination target of canceration according to determination 2.

The effectiveness of determination 2 is confirmed by the validation described above. Therefore, the determination of canceration can be more accurately carried out when the determination on the appropriateness of cell harvesting is configured by determinations 1, 2 as in the embodiment described above than when the determination on the appropriateness of cell harvesting is configured only by determination 1. The modifications described in FIGS. 15B and 15C also have the effects of the determination on the appropriateness of cell harvesting.

Figure 17B:
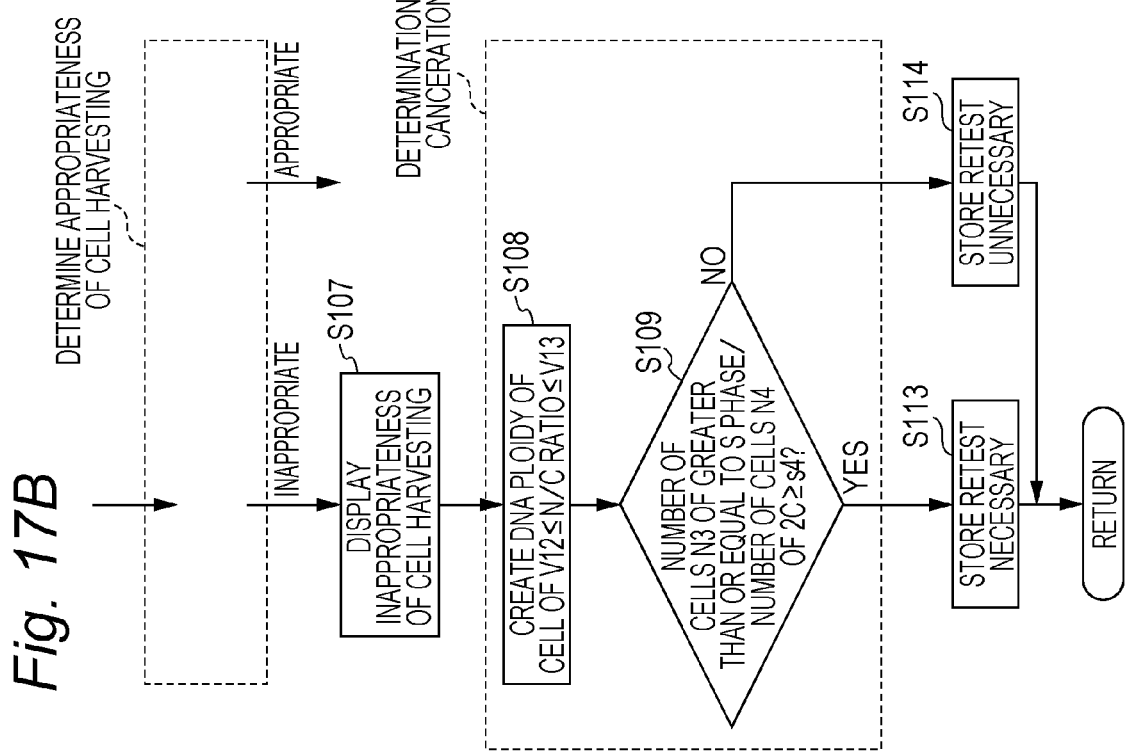
FIGS. 17A and 17B are flowcharts showing analysis processing in a data processing device according to the modification.
Figure 17A:
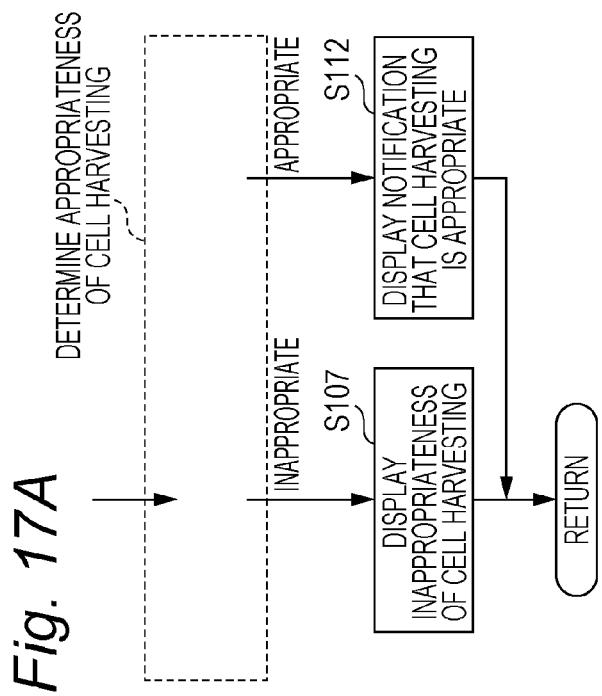

As shown in FIG. 9, the canceration information providing device 1 of the embodiment described above performs the determination on the appropriateness of cell harvesting and the determination of canceration, but the present invention may be applied to a device that performs only the determination on the appropriateness of cell harvesting. In this case, the flowchart of FIG. 9 is changed as in FIG. 17A. In FIG. 17A, the illustration of S101 to S103 and the content of the determination on the appropriateness of cell harvesting (S104 to S106) is omitted. In this case, when determined as appropriate in the determination on the appropriateness of cell harvesting (S105: NO, or S106: NO), the CPU 301 displays a notification that the harvesting of parabasal cells is appropriate (S112). Specifically, a dialogue showing "cell harvesting is appropriate" is displayed on the display section 32.

In the present embodiment, when determined as inappropriate in the determination on the appropriateness of cell harvesting, the processing is terminated without performing the determination of canceration and the output of canceration information of post-stages. However, even if determined as inappropriate in the determination on the appropriateness of cell harvesting, for example, the result of inappropriate cell harvesting such as "low reliability" and the like may be displayed (S107), and furthermore, the determination of canceration (S108, S109) may be carried out and the canceration information may be stored in the hard disc 304 (S113, S114), as shown in FIG. 17B. In FIG. 17B, the illustration of S101 to S103, the content of the determination on the appropriateness of cell harvesting (S104 to S106), and the post-stage processing (S108 to S111) of when determined as appropriate in the determination on the appropriateness of cell harvesting is omitted.

After the processing is carried out as in FIG. 17B, the determination of canceration is carried out regardless of the result of the determination on the appropriateness of cell harvesting, and hence the processing is simplified. Furthermore, since the determination of canceration is carried out even if determined as inappropriate in the determination on the appropriateness of cell harvesting, the determination result of canceration can be appropriately reviewed for the sample in which the harvesting of cell is not appropriately carried out. In the processing of FIG. 17B as well, if determined as inappropriate in the determination on the appropriateness of cell harvesting, the determination result of canceration is not output, and thus the information of low reliability can be prevented from being output in advance.

In the processing of FIG. 17B, the canceration information is merely stored and is not output, but the present invention is not limited to such an embodiment, and the canceration information may be stored and also output.

In the embodiment described above, the regions A3, A4 are set as shown in FIG. 10C, and the regions A5, A6 are set as shown in FIG. 10D. However, this is not the sole case, and the ranges of the regions A3 to A6 may be appropriately set to different values from the standpoints of sensitivity and specificity.

FIG. 18A is a diagram showing a state in which the boundary on the right side of the region A3 of FIG. 10C is extended toward the right direction. FIG. 18B is a diagram showing a state in which both the upper limit and the lower limit of the region A3 of FIG. 10C are eliminated. Thus, the region A3 may be set from the standpoints of sensitivity and specificity.

FIG. 18C is a diagram showing a state in which the right end of the region A6 of FIG. 10D is shortened. V21 and V23 of the region A6 of FIG. 18C are set such that V20 is included in the range between V21 and V23, and the width of the range between V21 and V23 is B, which is smaller than the width A of FIG. 10D. FIG. 18D is a diagram showing a state in which the left end of the region A5 of FIG. 10D is extended. The value V24 at the left end of the region A5 of FIG. 18D is set to have a value greater than V20 and smaller than V22 when V20 is included in the range between V21 and V22, and the width of the range between V21 and V22 is set as A. Thus, the regions A5, A6 may be set from the standpoints of sensitivity and specificity.

In the embodiment described above, whether or not the number of cells N2 is smaller than the threshold value s2 is first determined, and then whether or not the value obtained by dividing the number of cells N1 by the number of cells N2 is smaller than the threshold value s3 is determined in determination 2 of FIG. 9. However, instead, whether or not the value obtained by dividing the number of cells N1 by the number of cells N2 is smaller than the threshold value s3 may be determined first, and then whether or not the number of cells N2 is smaller than the threshold value s2 may be determined.

In the embodiment described above, the epidermal cell of the uterine cervix is the analyzing target, but other epidermal cells of buccal cells, bladder, pharynx, and the like, and furthermore, the epidermal cells of organs may be the analyzing target, and the determination of canceration may be performed on such cells.

In the embodiment described above, the N/C ratio is calculated as a ratio between the numerical value (size N of cell nucleus) indicating the width of the cell nucleus obtained based on the width of the waveform of the side fluorescence intensity, and the numerical value (size C of cell) indicating the width of the cell obtained based on the width of the waveform of the forward scattered light intensity. However, this is not the sole case, and the N/C ratio may be calculated as a ratio between the area of the cell nucleus and the area of the cell. In the embodiment described above, the numerical value (size C of cell) indicating the width of the cell is obtained based on the width of the waveform of the forward scattered light intensity. Thus, the size of the cell can be accurately represented even when the cell having a long shape in a predetermined direction is flowed through the flow cell.

In the embodiment described above, when determined as inappropriate in the determination on the appropriateness of cell harvesting, the dialogue D1 shown in FIG. 11A is displayed on the display section 32, but instead, a warning sound may be output from a speaker installed in the data processing device 3.

The embodiment of the present invention may be appropriately changed within a scope of the technical concept defined in the claims.

What is claimed is:

1. A cell analyzer comprising:
   a detecting section comprising an optical device that detects information of each cell from a measurement specimen containing cells harvested from an epithelial tissue including parabasal cells, wherein the epithelial tissue includes surface layer cells, intermediate layer cells, and the parabasal cells, where the intermediate layer cells are between the surface layer cells and the parabasal cells, and
   a controller comprising a CPU and a memory device programmed to:
   acquire a feature parameter of each cell based on the detected information,
   wherein the feature parameter includes a first parameter related to a size of a cell, and a second parameter related to a size of a cell nucleus, and;
   determine appropriateness of the cell harvesting of the parabasal cells based on the feature parameter,
   wherein the controller sorts the parabasal cells and cells in the surface layer cells and the intermediate layer cells based on the first parameter and the ratio of the second parameter with respect to the first parameter, and determines the appropriateness of the cell harvesting of parabasal cells based on the sorting result; and
   determine canceration of the parabasal cells based on the feature parameter,
   wherein the determination of appropriateness of the cell harvesting is performed independently from the determination of canceration.

2. The cell analyzer according to claim 1, further comprising an output section comprising an interface and a display that outputs information indicating that the cell harvesting is inappropriate when the controller has determined that the cell harvesting of parabasal cells is inappropriate.

3. The cell analyzer according to claim 2, wherein the controller acquires information related to canceration of the cell, and the controller does not control the output section to output the information related to the canceration of the cell when the controller has determined that the cell harvesting of parabasal cells is inappropriate.

4. The cell analyzer according to claim 1, further comprising a cell dispersion section comprising one of a shearing device or an ultrasonic device that disperses aggregated cells in the measurement specimen into individual cells; wherein the detecting section detects information of each cell from the dispersed measurement specimen.

5. The cell analyzer according to claim 1, wherein the controller calculates the concentration of the cells in the measurement specimen; and
   the analyzer comprises an aspiration section comprising an aspiration device that adjusts the liquid measure of the measurement specimen based on the calculated concentration.

6. The cell analyzer according to claim 1, wherein the controller classifies aggregated cells and non-aggregated cells in the measurement specimen based on the feature parameter, and determines the appropriateness of the cell harvesting of parabasal cells based on the non-aggregated cells.

7. The cell analyzer according to claim 1, wherein the detecting section includes a flow cell, through which the measurement specimen flows, and a light receiving unit configured to irradiate light on the measurement specimen flowing through the flow cell and receiving optical information from each cell contained in the measurement specimen, wherein the optical information is detected as the information of each cell.

8. The cell analyzer according to claim 7, wherein the detecting section detects scattered light information and fluorescence information as the information of each cell.

9. The cell analyzer according to claim 1, wherein the controller acquires information related to the number of parabasal cells based on the sorting result, and determines the appropriateness of the cell harvesting of parabasal cells based on the acquired information related to the number of parabasal cells.

10. The cell analyzer according to claim 1, wherein the controller acquires information related to the number of the parabasal cells and information related to the number of cells existing in the surface layer cells and the intermediate layer cells based on the sorting result, and determines the appropriateness of the cell harvesting of the parabasal cells based on the information related to the number of the parabasal cells and the information related to the number of cells in the surface layer cells and the intermediate layer cells than the parabasal cells.

11. The cell analyzer according to claim 10, wherein the controller determines the appropriateness of the cell harvesting of the parabasal cells based on a ratio between the information related to the number of the parabasal cells and the information related to the number of the surface layer cells and the intermediate layer cells than the parabasal cells.

12. The cell analyzer according to claim 1, wherein the epithelial tissue is an epithelial tissue of a uterine cervix.

13. A cell analyzer comprising:
 a detection section comprising an optical device that detects information of each cell from a measurement specimen containing cells harvested from an epithelial tissue including parabasal cells, wherein the epithelial tissue includes surface layer cells, intermediate layer cells, and the parabasal cells, where the intermediate layer cells are between the surface layer cells and the parabasal cells, and a controller comprising a CPU and a memory device programmed to:
 acquire a feature parameter of each cell based on the detected information,
 wherein the feature parameter includes a first parameter related to a size of a cell, and a second parameter related to a size of a cell nucleus;
 determine appropriateness of cell harvesting of the parabasal cells based on the feature parameter,
 wherein the controller sorts the parabasal cells and cells in the surface layer cells and the intermediate layer cells based on the first parameter and the ratio of the second parameter with respect to the first parameter, and determines the appropriateness of the cell harvesting of parabasal cells based on the sorting result;
 when the cell harvesting of the parabasal cells is appropriate, determine canceration of the parabasal cells based on the feature parameter; and
 when the cell harvesting of the parabasal cells is inappropriate, giving a notice without determining canceration of the parabasal cells.

* * * * *